United States Patent
Suzuki et al.

(10) Patent No.: US 10,350,118 B2
(45) Date of Patent: Jul. 16, 2019

(54) ABSORBENT ARTICLE WITH NEW LEG GATHERS

(75) Inventors: Migaku Suzuki, Chigasaki (JP); Yoshio Hirai, Tokyo (JP)

(73) Assignee: DAIO PAPER CORPORATION, Shikokuchuo (JP)

( * ) Notice: Subject to any disclaimer, the term of this patent is extended or adjusted under 35 U.S.C. 154(b) by 757 days.

(21) Appl. No.: 14/422,312

(22) PCT Filed: Aug. 20, 2012

(86) PCT No.: PCT/JP2012/071000
§ 371 (c)(1),
(2), (4) Date: Feb. 18, 2015

(87) PCT Pub. No.: WO2014/030201
PCT Pub. Date: Feb. 27, 2014

(65) Prior Publication Data
US 2015/0216738 A1  Aug. 6, 2015

(51) Int. Cl.
*A61F 13/15* (2006.01)
*A61F 13/494* (2006.01)
(Continued)

(52) U.S. Cl.
CPC .. *A61F 13/49473* (2013.01); *A61F 13/49019* (2013.01); *A61F 13/49406* (2013.01);
(Continued)

(58) Field of Classification Search
CPC .......... A61F 13/49019; A61F 13/49406; A61F 13/49473; A61F 2013/49041;
(Continued)

(56) References Cited

U.S. PATENT DOCUMENTS

2002/0010453 A1* 1/2002 Mishima ............... A61F 13/495
 604/385.19
2007/0088306 A1 4/2007 Sugiyama et al.
(Continued)

FOREIGN PATENT DOCUMENTS

EP 2 815 732 A1 12/2014
JP H06-78952 A 3/1994
(Continued)

OTHER PUBLICATIONS

Nov. 20, 2012 Written Opinion issued in International Application No. PCT/JP2012/071000.
(Continued)

*Primary Examiner* — Bradley H Philips
(74) *Attorney, Agent, or Firm* — Oliff PLC

(57) ABSTRACT

Absorbent article includes: a sheet-type leakage-preventing body; absorbent body on the leakage-preventing body top; pair of left and right floating leg gathers (FLGs) on the absorbent body top to extend in longitudinal direction from front end absorbent article main body, traversing a front main section, crotch part, and rear main section, to rear end. Each FLGs have top and trailing parts adjoining the top part. Left and right FLGs arrange so top parts face inwards and trailing parts face outwards. Front and rear ends FLGs are joined respectively to the vicinity of the absorbent article main body front and rear end. Trailing part trails downwards from top part towards the absorbent body. Left and right FLGs join in vicinity of trailing part lower end to the absorbent article main body and/or absorbent body surface forming front and rear pockets distance from the absorbent body surface in the crotch part vicinity.

19 Claims, 10 Drawing Sheets

(51) Int. Cl.
*A61F 13/49* (2006.01)
*A61F 13/495* (2006.01)

(52) U.S. Cl.
CPC ... *A61F 13/495* (2013.01); *A61F 2013/49041* (2013.01); *A61F 2013/4944* (2013.01); *A61F 2013/4951* (2013.01); *A61F 2013/4953* (2013.01); *A61F 2013/4956* (2013.01); *A61F 2013/4958* (2013.01)

(58) Field of Classification Search
CPC .......... A61F 2013/4953; A61F 13/4944; A61F 13/495; A61F 13/4951; A61F 13/4953; A61F 13/4958; A61F 13/4956

See application file for complete search history.

(56) References Cited

U.S. PATENT DOCUMENTS

| | | | |
|---|---|---|---|
| 2009/0036852 | A1 | 2/2009 | Suzuki et al. |
| 2010/0221407 | A1* | 9/2010 | Tee, Jr. ............... A61F 13/4753 427/2.3 |

FOREIGN PATENT DOCUMENTS

| | | |
|---|---|---|
| JP | 2002-035031 A | 2/2002 |
| JP | 2012-518496 A | 8/2012 |

OTHER PUBLICATIONS

Oct. 23, 2012 Office Action issued in Japanese Application No. JP2012-538119.
Nov. 20, 2012 International Search Report issued in Application No. PCT/JP2012/071000.
Mar. 31, 2016 Extended Search Report issued in European Patent Application No. 12883343.1.

* cited by examiner (A)

(B)

(C)

(D)

(E)

(F)

(A)

(B)

(A)

(B)

(C)

(A)

(B)

(A)

(B)

ABSORBENT ARTICLE WITH NEW LEG GATHERS

FIELD OF THE INVENTION

The present invention relates to an absorbent article with new leg gathers.

BACKGROUND ART

Absorbent articles such as paper diapers (for infants and adults), sanitary napkins, incontinence articles, training pants or the like are articles that absorb bodily fluids, such as urine excreted from a wearer, by means of an absorber that makes use of a super absorbent polymer (hereinafter referred to as an "SAP"), fluffy pulp or the like.

Conventional absorbent articles prevent leakage by closely attaching an absorber to the surface of the body of a wearer without any gap and by transferring the excreted bodily fluids from the surface of the absorber to the inside thereof to be absorbed therein.

Such closely-attached state of the absorber to the body of the wearer is achieved by applying a "pressing force from the exterior" to the absorber. This will be described in more detail by taking an infant's diaper as an example.

For infant's diapers, in diapers where a "pressing force from the exterior" occurs, various stretchable materials (similar to those used in pantyhose, supporters, competition swimsuits and the like) are arranged at various parts. Especially in recent years, for tapeless underpants-type diapers which have become a main trend for infant' diapers, since they are mainly intended for infants when their body movement becomes active (approximately 6 kg or more in body weight), it is necessary to make use of a stretchable material.

In general, the following stretchable materials are used for underpants-type diapers:

(1) A waist gather band (waist part stretchable body): the waist gather band serves as a fixing band that connects a front end part and a rear end part of a diaper body to each other, attaches the diaper closely around the waist and prevents the diaper from sliding down;

(2) Shining gathers or trunk gathers (trunk part maintaining stretchable body): the shining or trunk gathers are present so as to cover each of a back surface and a ventral surface of the diaper and exhibit functions of pressing the absorber in the vicinity of the back surface and in the vicinity of the ventral surface against the surface of the wearer's body; and (3) Leg gathers (leg part stretchable body): the leg gathers provide sealing, in the vicinity of the crotch part, so that no gap is formed between the diaper body and the wearer's body and play a role of a dam (bank) that prevents leakage from the side surfaces of the absorber. The leg gathers are classified into the following three types depending on their roles, and each type may be used alone or two or more types may be used in combination.

(3a) First inner leg gather (ILG): the first ILG is provided above the absorber or on a side edge of the absorber, includes a stretchable head part and a leg part made of a non-woven fabric, and usually has a standing geometry.

(3b) Second inner leg gather (ILG): the second ILG is provided on the side edge of the absorber or on the exterior thereof, includes a stretchable head part and a leg part made of a non-woven fabric, and usually has a standing geometry.

(3c) Outer leg gather (OLG) or gusset gather: the OLG or gusset gather is provided by sandwiching a stretchable material by a top sheet and a leak preventer from both sides at the side edge of the diaper body, and it is usually flat; however, it is folded on the inward side, in some cases, to be used in a standing geometry.

SUMMARY OF THE INVENTION

Problems to be Solved by the Invention

When the above-described stretchable materials are used in a form where a strong tension concentrates, as in a wide rubber band, they give the wearer a feeling of restraint and leave marks, and thus, in general, improvement efforts have been made such as to arrange a plurality of fine polyurethane filaments in parallel to disperse tension. However, current diapers are still greatly associated with a feeling of restraint for the wearer, both physically and psychologically.

In addition, since conventional diapers achieve the closely-attached state of the absorber to the wearer's body by a "pressing force from the exterior," hot and stuffy state and rashes are likely to occur.

Accordingly, it is an object of the present invention to provide an absorbent article that has less of a feeling of restraint at the time of wearing and in which the occurrence of hot and stuffy state and rashes is suppressed.

Means for Solving the Problems

In order to achieve the object set forth above, the present inventors contemplated achieving an absorbent article that has less of a feeling of restraint at the time of wearing and in which the occurrence of hot and stuffy state and rashes is suppressed, by means of a new concept, without using a "pressing force from the exterior."

As a result of diligently conducting research, the present inventors have found that: by providing a pair of right and left floating leg gathers (hereinafter referred to as "FLGs"), which include head parts and hanging parts that connect to the head parts and which are configured such that a front end part and a rear end part of the FLG are respectively coupled to in the vicinity of a front end part and in the vicinity of a rear end part of the absorbent article body and such that the hanging parts hang down from the head parts toward the absorber, as a pair of FLGs arranged, above the absorber, from a front end part to a rear end part of the absorbent article body in the length direction via a front body, a crotch part and a rear body; and by connecting at least parts of the hanging parts of the pair of right and left FLGs to each other in the vicinity of the lower end parts thereof so as to form a transferring passage for bodily fluids on the inner surface sides of the hanging parts, the FLGs and the absorber are spaced apart at the time of wearing the absorbent article, and thus, a feeling of restraint at the time of wearing is reduced and contact of the urine or feces excreted onto the absorber with the wearer's skin is effectively suppressed and thus, the occurrence of hot and stuffy state and rashes is suppressed, and then completed the present invention.

The present invention focuses especially on a skin contact member and an absorber member, among the members configuring the absorbent article.

(1) In the conventional absorbent article, both the absorber and the gather that stands up therefrom are pressed against the wearer's skin, whereas in the present invention, a "skin contact member which functions by being constantly and closely attached in a soft manner to the skin of the wearer on the side edges of the bodily fluid excretory organ" and an "absorber member which is rigid and requires a form retaining property" are functionally separated.

(2) The above-described "absorber member" is physically spaced apart from the surface of the wearer's body.

(3) In regard to the above-described "skin contact member," a pair of FLGs having a pair of right and left head parts and a pair of right and left hanging parts that hangs down from the head parts toward the absorber member, are provided as a separate entity.

Based on the above, the present invention provides a new absorbent article in which the absorber is not pressed against the wearer's body surface like in the conventional absorbent article and which is capable of sufficiently fulfilling the absorption function of the absorber while keeping the absorber spaced apart from the wearer's body surface.

Namely, the present invention provides the following (1) to (19):

(1) An absorbent article including:

a leak preventer in sheet form;

an absorber capable of absorbing a bodily fluid, wherein at least one layer thereof is arranged above the leak preventer; and a pair of right and left floating leg gathers that are arranged, above the absorber, from a front end part to a rear end part in a length direction of a body of the absorbent article via a front body, a crotch part and a rear body, wherein the floating leg gather has a head part and a hanging part that connects to the head part, wherein the head parts of the pair of right and left floating leg gathers are arranged to face inward and the hanging parts thereof are arranged to face outward, wherein a front end part and a rear end part of the floating leg gather respectively couple to in the vicinity of the front end part and in the vicinity of the rear end part of the body of the absorbent article, the hanging part being configured to hang down from the head part toward the absorber, wherein the pair of right and left floating leg gathers: form a front part pocket by being coupled to the body of the absorbent article and/or to a surface of the absorber in the vicinity of lower end parts of the hanging parts thereof, from the front end part to the front body in the front-rear direction; form a rear part pocket by being coupled to the body of the absorbent article and/or the surface of the absorber in the vicinity of the lower end parts of the hanging parts thereof, from the rear end part to the rear body in the front-rear direction; and are spaced apart from the surface of the absorber in the vicinity of the crotch part.

(2) The absorbent article according to (1), wherein the head parts of the pair of right and left floating leg gathers are arranged so as to oppose each other in the vicinity of a center part in the lateral direction.

(3) The absorbent article according to (2), wherein a space between the head parts of the pair of right and left floating leg gathers is covered with means of a leak prevention sheet, at least partially in the front-rear direction, the head parts being opposed.

(4) The absorbent article according to (3), wherein a part in which the space between the head parts of the pair of right and left floating leg gathers is covered is present at least from the front end part of the body of the absorbent article to the front body thereof.

(5) The absorbent article according to (3) or (4), wherein a part in which the space between the head parts of the pair of right and left floating leg gathers is covered is present at least from the rear end part of the body of the absorbent article to the rear body thereof.

(6) The absorbent article according to (1), wherein the head parts of the pair of right and left floating leg gathers are arranged so as to overlap with each other, in the vicinity of a center part in the lateral direction, at least partially in the front-rear direction.

(7) The absorbent article according to (6), wherein parts of the head parts of the pair of right and left floating leg gathers that overlap with each other in the vicinity of the center part in the lateral direction are present at least from the front end part of the body of the absorbent article to the front body thereof.

(8) The absorbent article according to (6) or (7), wherein parts of the head parts of the pair of right and left floating leg gathers that overlap with each other in the vicinity of the center part in the lateral direction are present at least from the rear end part of the body of the absorbent article to the rear body thereof.

(9) The absorbent article according to any one of (1) to (8), wherein the hanging parts of the pair of right and left floating leg gathers are connected to each other in the vicinity of the lower end part thereof in the vicinity of the crotch part so as to form a transferring passage for bodily fluids on the inner surface sides of the hanging parts.

(10) The absorbent article according to (9), wherein the hanging parts of the pair of right and left floating leg gathers are connected to each other by being respectively coupled to a hanging part support sheet in the vicinity of the lower end parts thereof in the vicinity of the crotch part and wherein the transferring passage for bodily fluids is formed by means of the hanging parts and the hanging part support sheet.

(11) The absorbent article according to (9) or (10), wherein the transferring passage for bodily fluids further extends from the crotch part to the front body.

(12) The absorbent article according to (11), wherein the transferring passage for bodily fluids connects to the front part pocket.

(13) The absorbent article according to any one of (9) to (12), wherein the transferring passage for bodily fluids further extends from the crotch part to the rear body.

(14) The absorbent article according to (13), wherein the transferring passage for bodily fluids connects to the rear part pocket.

(15) The absorbent article according to any one of (9) to (14), wherein the transferring passage for bodily fluids couples to the surface of the absorber at a front end part thereof and/or a rear end part thereof.

(16) The absorbent article according to any one of (1) to (15), further including a pair of right and left standing leg gathers which are arranged outward of the pair of right and left floating leg gathers, wherein the standing leg gather has a head part and a leg part that continues to the head part, a lower end part of the leg part being coupled to the body of the absorbent article and standing up therefrom.

(17) The absorbent article according to (16), wherein the hanging part of the floating leg gather and the leg part of the standing leg gather are coupled to each other.

(18) The absorbent article according to (17), wherein a part where the hanging part of the floating leg gather and the leg part of the standing leg gather are coupled to each other is present at least in the rear body.

(19) The absorbent article according to (17) or (18), wherein the part where the hanging part of the floating leg gather and the leg part of the standing leg gather are coupled to each other is present at least in the vicinity of the crotch part.

Effect of the Invention

An absorbent article according to the present invention has a less of a feeling of restraint at the time of wearing and in which the occurrence of hot and stuffy state and rashes is suppressed.

BRIEF DESCRIPTIONS OF THE DRAWINGS

FIG. 1 contains schematic diagrams illustrating an example of an absorbent article according to the present invention.

FIG. 2 is a schematic diagram illustrating an example of an absorbent article according to the present invention.

FIG. 3 contains schematic diagrams illustrating an embodiment of an absorbent article according to the present invention.

FIG. 4 contains schematic plan views of various hanging part support sheets.

Figure 7:
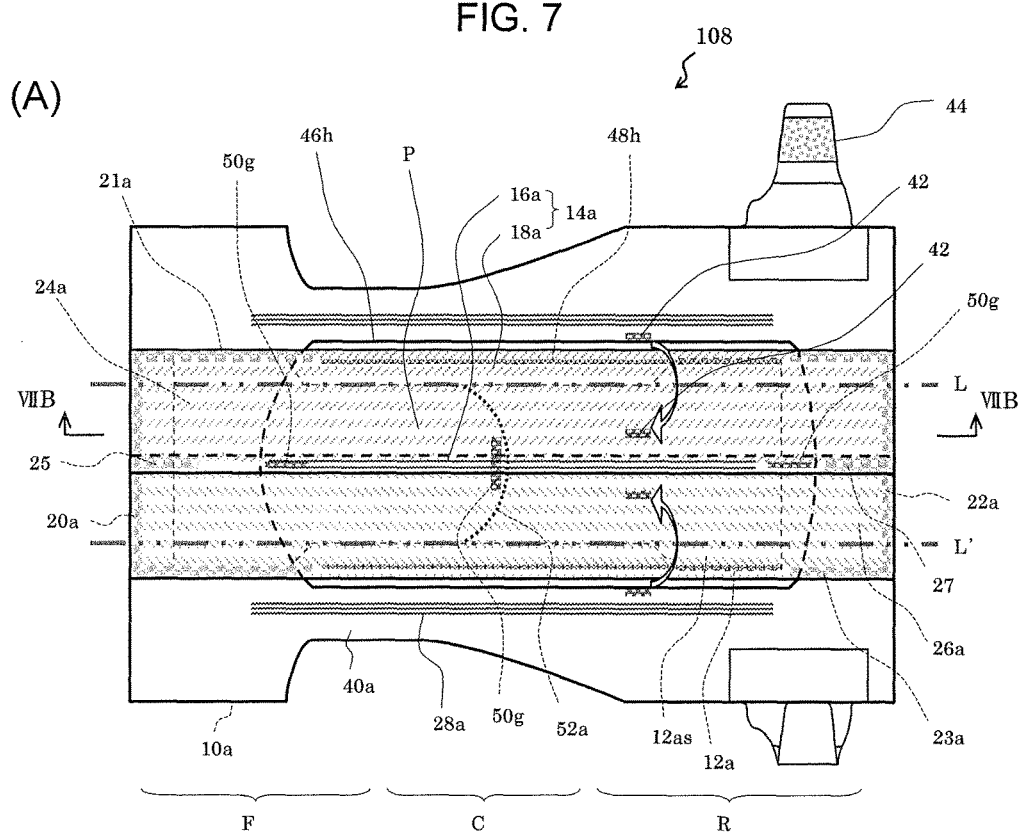
Figure 7:
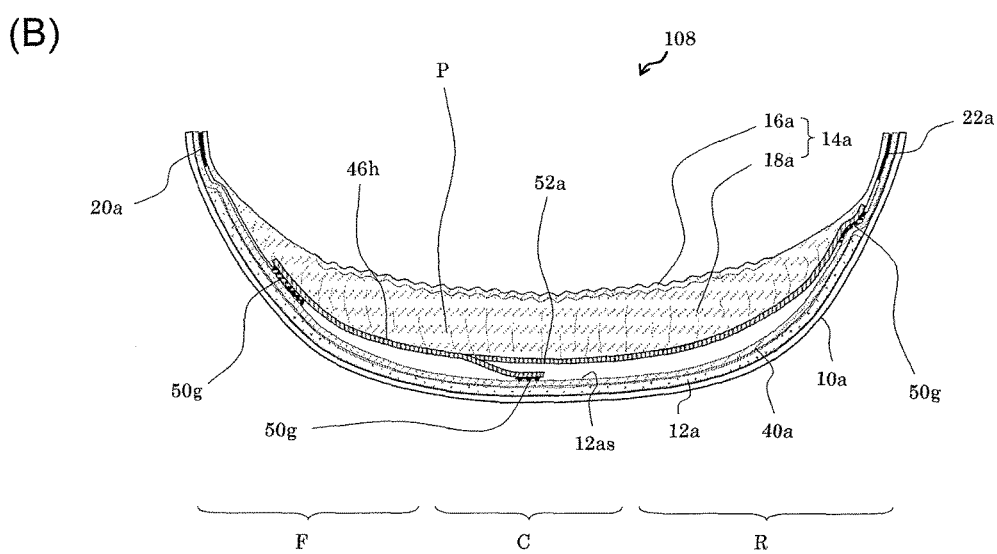

FIG. 7 contains schematic diagrams of a further embodiment of the absorbent article according to the present invention.

Figure 8:
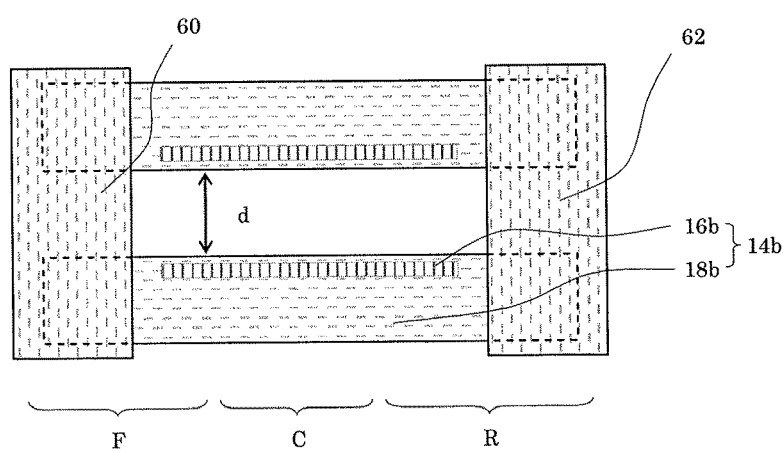
Figure 8:
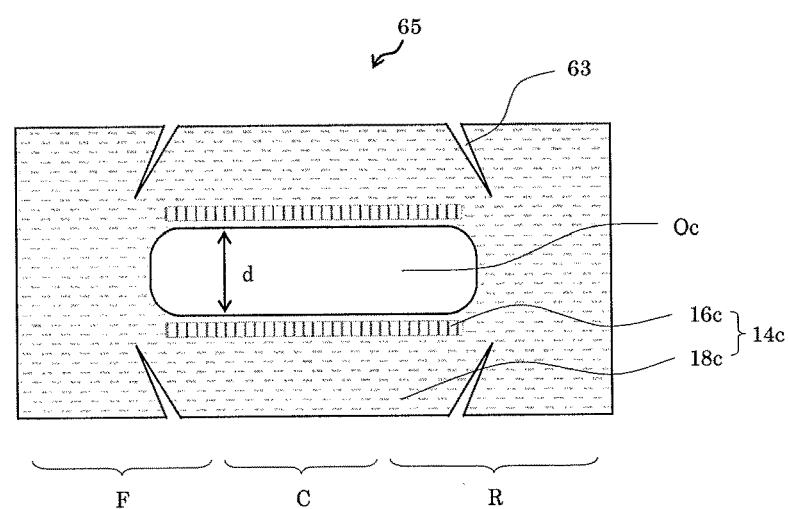
Figure 8:
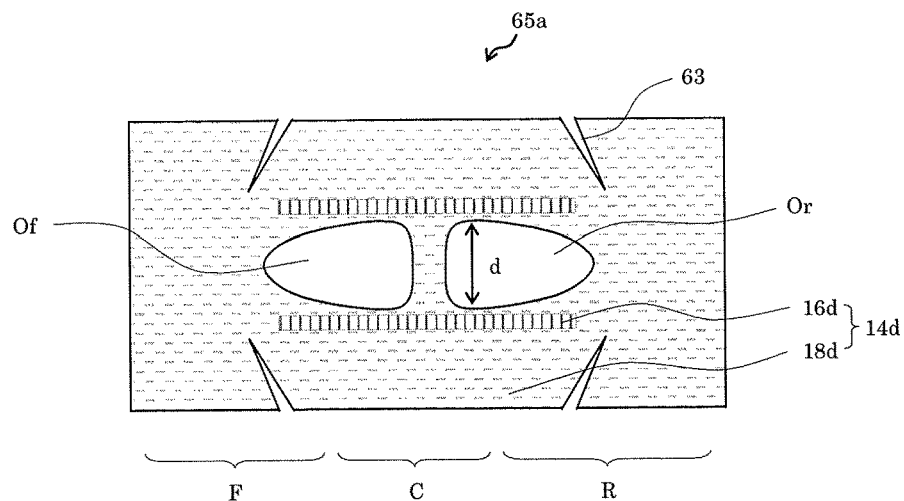

FIG. 8 contains schematic plan views illustrating various examples of FLGs in which a space between the opposing head parts is covered with means of a leak prevention sheet, at least partially in the front-rear direction.

Figure 9:
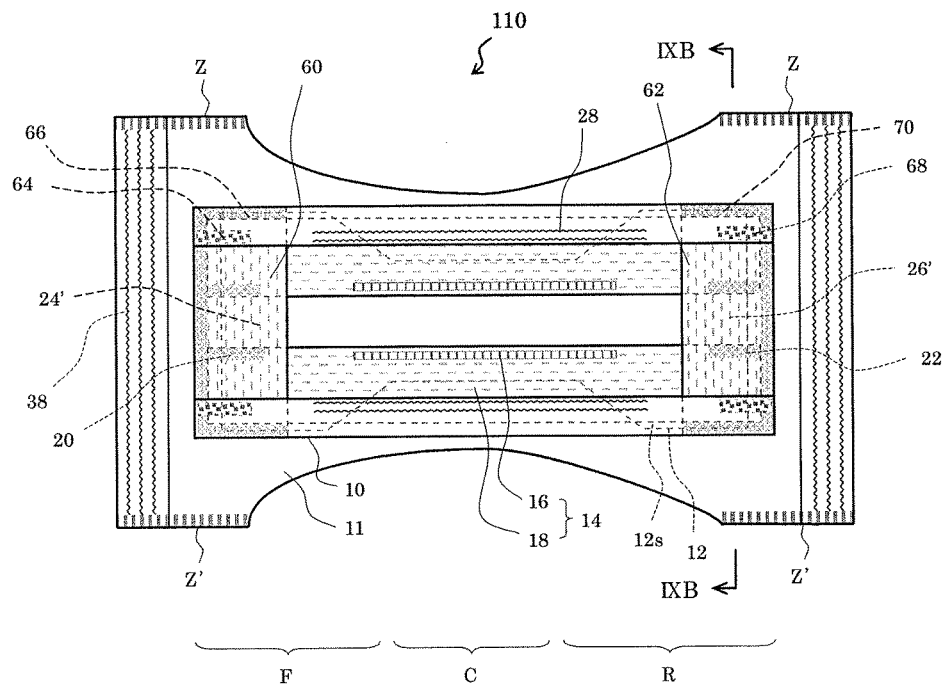
Figure 9:
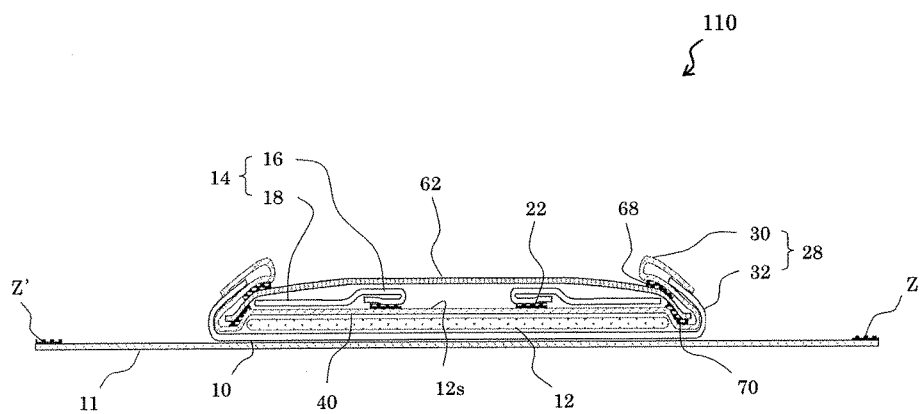

FIG. 9 contains schematic diagrams illustrating a further example of an absorbent article according to the present invention.

Figure 10:
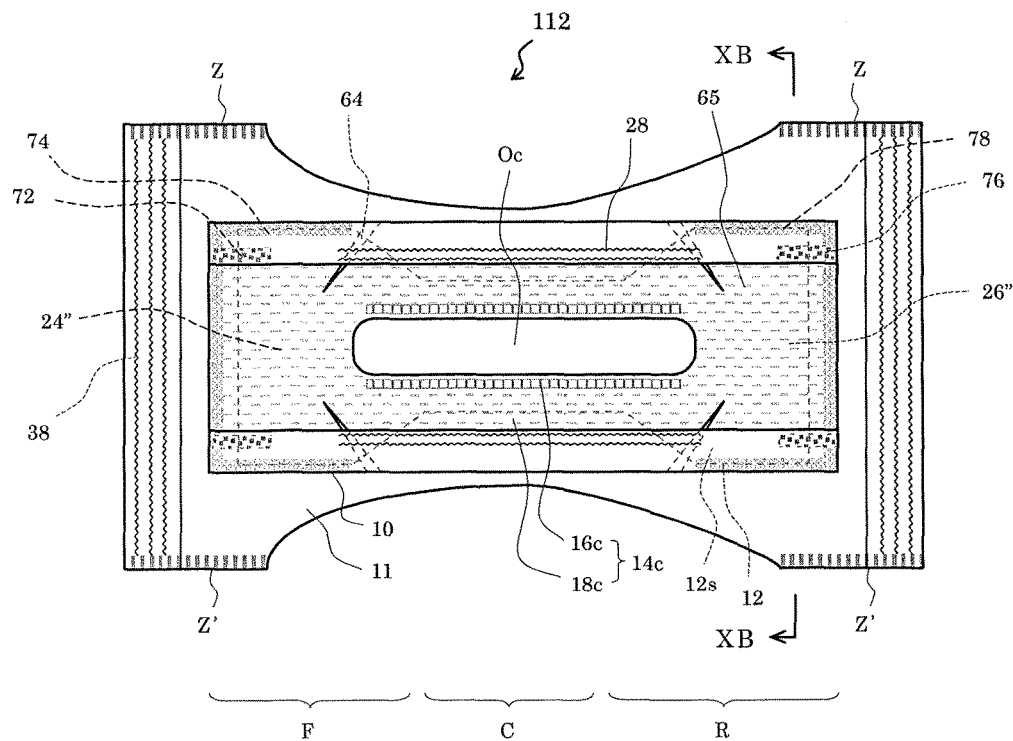
Figure 10:
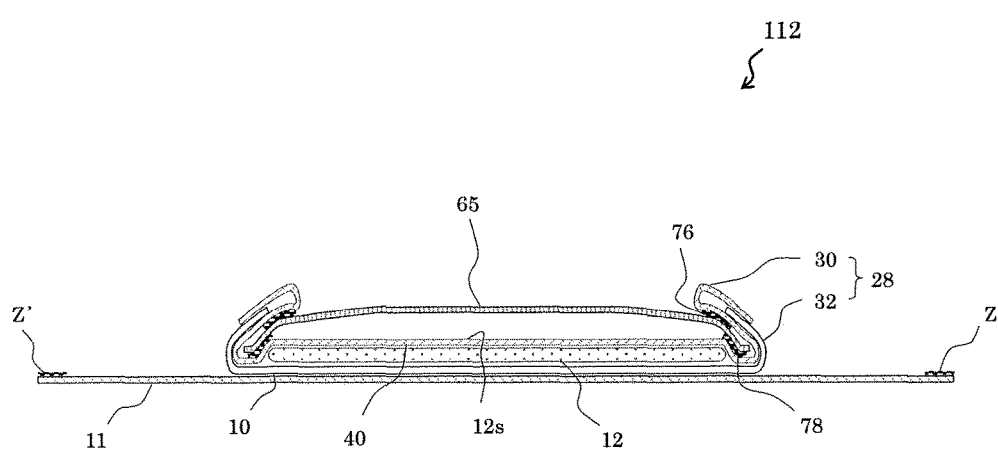

FIG. 10 contains schematic diagrams illustrating a further example of an absorbent article according to the present invention.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views and perspective views among the attached drawings, the front side of the absorbent article, etc. is illustrated such that it is positioned on the left side of the corresponding drawing. In the respective longitudinal sectional views among the attached drawings, the front side of the absorbent article, etc. is illustrated such that it is positioned on the left side of the corresponding drawing.

In addition, in the present specification, an "absorbent article body" collectively refers to a leak preventer, a top sheet that can be provided above the leak preventer and various other members that can be provided to the absorbent article, all of which are constituent members of the absorbent article. In accordance with this, when the absorbent article is a diaper, the absorbent article body will be referred to as a diaper body.

Moreover, in the present specification, an "absorber surface" refers to a surface of an absorber when it is exposed, and to a surface of a diffusion sheet, acquisition sheet, top sheet or the like when the absorber is covered with such diffusion sheet, acquisition sheet, top sheet or the like.

Figure 1:
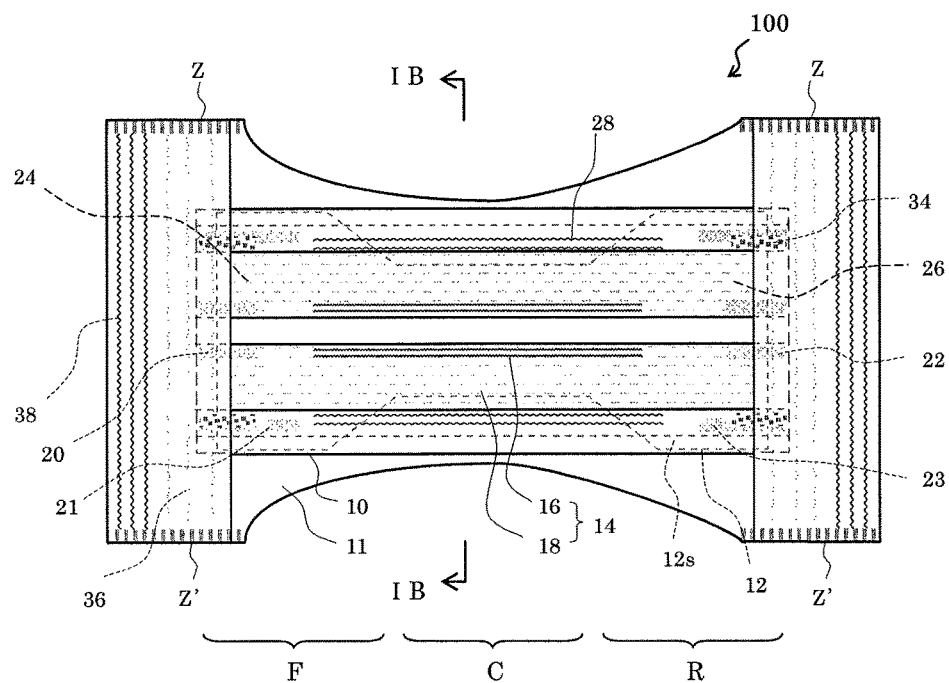
Figure 1:
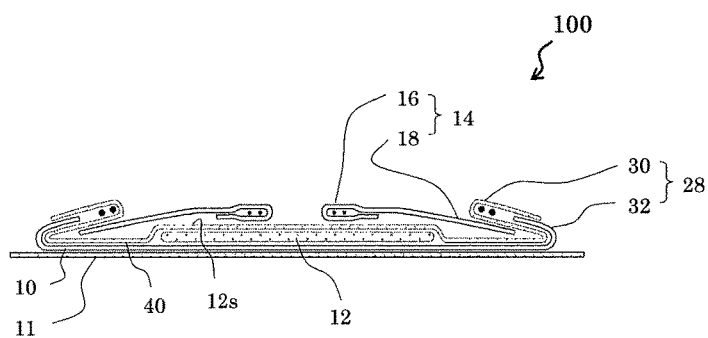
Figure 1:
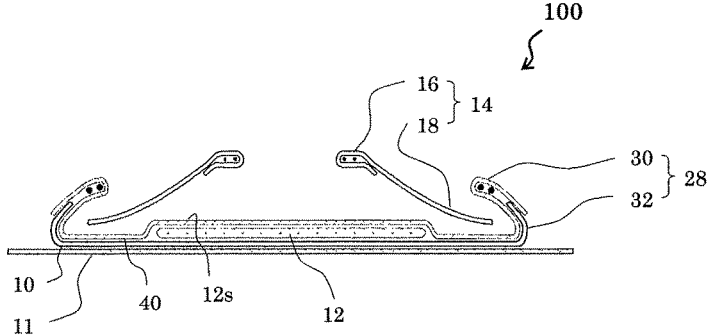
Figure 2:
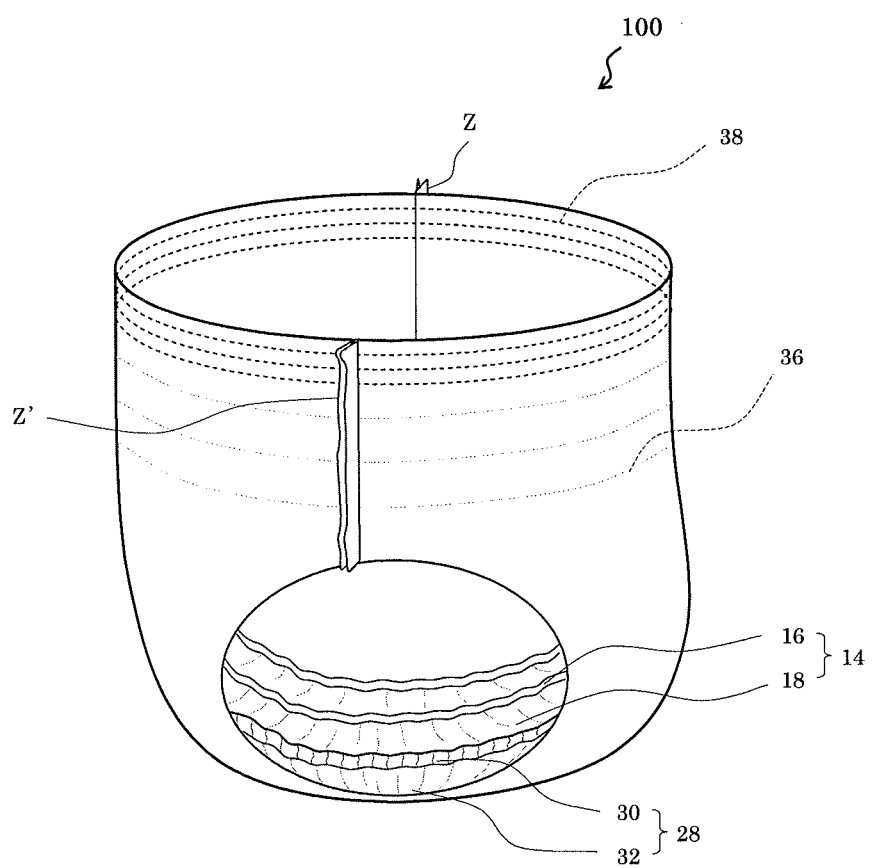

FIGS. 1 and 2 contain schematic diagrams illustrating an example of an absorbent article according to the present invention. FIG. 1(A) is a developed plan view which schematically shows the state in which an absorbent article, in the form of an underpants-type diaper, is cut along the right and left side parts (denoted with "Z" and "Z"' in the figure) of the waist gather and in which stress is applied to the absorbent article such that it is pulled in the front-rear direction and the lateral direction to be developed into a substantially planar form. FIG. 1(B) is a lateral end view along line IB-IB in FIG. 1(A) in the above-described state. FIG. 1(C) is a lateral end view along line IB-IB in FIG. 1(A) when stress is not applied to the absorbent article (i.e. in a relaxed state). FIG. 2 is a perspective view thereof.

Absorbent article 100 according to the present invention shown in FIGS. 1 and 2 is configured as an underpants-type diaper and is, basically provided with: leak preventer 10 in sheet form; absorber 12 capable of absorbing a bodily fluid, wherein at least one layer thereof is arranged above leak preventer 10; and a pair of right and left FLGs 14 arranged, above absorber 12, from a front end part of the absorbent article body to a rear end part thereof in a longitudinal direction, via front body F, crotch part C and rear body R.

Materials that are generally used as a back sheet can be used for the materials of leak preventer 10. In particular, a resin film made of, for example, PE, PP, PET, EVA or the like and a bodily fluid impermeable sheet such as a foam sheet made of the resin described above can be used. For the bodily fluid impermeable sheet, a sheet having air permeability, such as an air permeable sheet or the like may be preferably used.

In addition, when the above-described resin film is used, a multilayered sheet of such film and a non-woven fabric may be used in order to improve the texture and appearance. In this case, a spunbond (SB) or thermalbond non-woven fabric having a relatively low basis weight (for example, an air-through type) or the like may preferably be used as the non-woven fabric.

Moreover, a multilayered sheet of such resin film and an absorber in sheet form, which is described below, may also be used.

Further, a high water-resistant non-woven fabric may also be used. Examples of such high water-resistant non-woven fabric include an SMS non-woven fabric having a degree of water resistance of 100 mm $H_2O$ or more and an SMS non-woven fabric in which pores in a non-woven web are filled with microfibrillated cellulose (MFC) or wax so as to provide such fabric with water resistance. In this case, a high water-resistant non-woven fabric may be used alone or may also be used as a multilayered sheet of the film and such high water-resistant non-woven fabric.

Leak preventer 10 is in sheet form; however, it is not particularly limited in terms of shape as long as it envelopes absorber 12, or the like, above itself and is capable of being arranged with FLGs 14 thereon.

In absorbent article 100, external covering sheet 11 is provided on the underside of leak preventer 10.

External covering sheet 11 is a member that is used in an underpants-type diaper and that bears a fitting function of enfolding the wearer's body. Specifically, a sheet-form member forming the respective parts of front body F, crotch part C and rear body R is used.

In an underpants-type diaper such as absorbent article 100, since leak preventer 10 prevents the leakage of urine or the like, it is unnecessary to use fluid impermeable materials for external covering sheet 11. For example, for external covering sheet 11, any external covering sheet that is used in publicly-known conventional absorbent articles may be used. In particular, a non-woven fabric configured by synthetic fibers made of, for example, polyethylene, polypropylene, polyester, or other thermoplastic resin may be used as external covering sheet 11.

In absorbent article 100, two pieces of non-woven fabric, which are external covering sheet 11, configures shining gather 36 by sandwiching a stretchable member (for example, a polyurethane filament). Shining gathers 36 are provided at positions in which the abdominal area and the back area of the wearer are covered at the time of wearing. In the present invention, the configuration of the shining gathers is not particularly limited and, for example, a publicly-known conventional configuration of the shirring gathers may be used.

Absorber 12 used in the present invention is not particularly limited, as long as it is capable of absorbing a bodily fluid, and any absorber used in publicly-known conventional absorbent articles may be used. Examples such as: pulverized wood pulp; an absorber in which pulverized wood pulp and granular or powdery SAP are mixed and shaped into a mat; a sheet-like absorber shaped into a thin sheet and having SAP as a primary component, or the like, may be used. These absorbers keep the shape thereof and at the same time prevent the generation and droppage of fine powder from pulp and SAP. Thus, in general, the absorbers are covered with a core wrapping material made of tissue paper, a non-woven fabric, a perforated film, or the like. In the present specification, when a core wrapping material is used, such core wrapping material is also inclusively referred to as an "absorber."

An absorber in sheet form excels in morphological stability and capability of SAP droppage prevention, etc.

Among various types of absorber in sheet form, a super absorbent sheet containing 50 weight % or more, preferably 60 weight % or more, or more preferably 70 weight % or more of SAP is preferred. In addition, from the perspective of stability, etc. of the super absorbent sheet, the content of SAP therein is preferably 95 weight % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, pulverized wood pulp and SAP are mixed and a binder is added to shape the mixture into a sheet form and then a super absorbent sheet is obtained. As examples of a super absorbent sheet obtained through this process, NOVATHIN (US registered trademark) manufactured by Rayonier Inc. in the US, B-SAP manufactured by Oji Kinocloth Co., Ltd., or the like, are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (registered trademark) manufactured by Japan Absorbent Technology Institute is known.

Other examples of the super absorbent sheet include: a super absorbent sheet obtained through a process involving having a raised non-woven fabric carry a large amount of SAP and fixing the SAP with a hot melt binder, an emulsion binder, a water soluble fiber, or the like; a super absorbent sheet obtained through a process involving mixing fibrous SAP with a PET (polyethylene terephthalate) fiber and shaping the mixture into a web; and an SAP sheet obtained by providing tissues above and below an SAP layer.

At least one layer of absorber 12 is arranged above leak preventer 10. Namely, absorber 12 may be comprised of one layer or two or more layers (multilayer).

In addition, absorber 12 may be arranged in a folded condition.

A pair of right and left FLGs 14 are arranged, above absorber 12, from a front end part of the absorbent article body to a rear end part thereof in a length direction, via front body F, crotch part C and rear body R. The FLGs may be provided by being coupled to the leak preventer, may be provided by being coupled to the top sheet or the other members provided above the leak preventer, or may be provided by being coupled to a plurality of members.

FLG 14 includes head part 16 and hanging part 18 that connects to head part 16. FLG 14 is, for example, configured by having a stretchable member (for example, two parallel polyurethane filaments shown in FIG. 1) therein. For a pair of right and left FLGs 14, head parts 16 are arranged to face inward and hanging parts 18 are arranged to face outward.

A front end part and a rear end part of FLG 14 respectively couple to in the vicinity of a front end part and in the vicinity of a rear end part of the absorbent article body. Specifically, both the front end part and the rear end part of head part 16 of FLG 14 (i.e. the parts in FIG. 1(A) where the polyurethane filaments are not present) couple to surface 12s of absorber 12 at front end coupling part 20 and rear end coupling part 22. In addition, both the front end part and the rear end part of hanging part 18 of FLG 14 couple to surface 12s of absorber 12 at front end coupling part 21 and rear end coupling part 23. In this way, hanging part 18 is configured to hang down from head part 16 toward absorber 12 (see FIG. 1(C)). The length in the front-rear direction of front end coupling part 21 and rear end coupling part 23 is relatively longer than that of front end coupling part 20 and rear end coupling part 22. The coupling method is not particularly limited and, for example, the coupling method may be achieved by means of an adhesive.

Most of FLG 14 (i.e. the part except for the parts corresponding to front end coupling part 20, rear end coupling part 22, front end coupling part 21 and rear end coupling part 23) is not coupled to surface 12s of absorber 12.

Hanging part 18 hangs down from head part 16 in curtain form and it does not stand up by being coupled to, fixed to and supported by the absorber (or the top sheet covering the absorber) as in conventional ILGs, but rather, in the vicinity of crotch part C, hanging part 18 is spaced apart from surface 12s of absorber 12 and floats from surface 12s of absorber 12. Since such new FLG 14 has a floating configuration as described above, it will be herein referred to as a floating leg gather (FLG). Such floating configuration may be realized by making, for example, the length between front end coupling parts 20, 21 and rear end coupling parts 22, 23 in FLG 14 shorter than the length between the front end coupling parts 20, 21 and rear end coupling parts 22, 23 in leak preventer 10.

The pair of right and left FLGs 14 couple to surface 12s of absorber 12 in the vicinity of the lower end parts of hanging parts 18 thereof, from the front end part to front body F in the front-rear direction, so as to form a pair of right and left front part pocket 24, and also couple to surface 12s of absorber 12 in the vicinity of the lower end parts of hanging parts 18 thereof, from the rear end part to rear body R in the front-rear direction, so as to form a pair of right and left rear part pocket 26.

More specifically, front part pocket 24 is an enclosed space formed by FLG 14 and surface 12s of absorber 12, being joined to each other at the respective locations including (1) front end coupling part 20 where head part 16 of FLG 14 and surface 12s of absorber 12 are coupled to each other, (2) front end coupling part 21 where hanging part 18 of FLG 14 and surface 12s of absorber 12 are coupled to each other, and (3) a coupling part between FLG 14 and a covered part of waist gather 38.

In addition, rear part pocket 26 is an enclosed space formed by FLG 14 and surface 12s of absorber 12, being joined to each other at the respective locations including (1) rear end coupling part 22 where head part 16 of FLG 14 and surface 12s of absorber 12 are coupled to each other, (2) rear end coupling part 23 where hanging part 18 of FLG 14 and surface 12s of absorber 12 are coupled to each other, and (3) a coupling part between FLG 14 and a covered part of waist gather 38.

In the present invention, the front part pocket may be configured by the hanging part of the FLG being coupled to the absorbent article body, rather than the hanging part of the FLG being coupled to the surface of the absorber, or it may be configured by the hanging part of the FLG being coupled to both the absorbent article body and the surface of the absorber.

At the time of wearing, head parts 16 of FLGs 14 make contact with the wearer's skin but keep a spaced-apart state from surface 12s of absorber 12.

Absorbent article 100 according to the present invention is further provided with a pair of right and left standing leg gathers (hereinafter referred to as "SLG") 28, which are arranged outward of the pair of right and left FLGs 14.

SLG 28 includes head part 30 and leg part 32 that connects to head part 30, and a lower end part of leg part 32 couples to leak preventer 10 via top sheet 40 and stands up therefrom. Specifically, head part 30 of SLG 28 is configured by folding back top sheet 40, which covers the entire absorbent article body including surface 12s of absorber 12, at the right and left edge parts thereof, in such a manner so as to include a stretchable material on the inner side thereof. Leg part 32 is configured by top sheet 40 and leak preventer 10.

SLG 28 is provided such that it is folded back so as to cover hanging part 18 of FLG 14 along the front-rear direction of absorbent article 100, and a front end and a rear end thereof are coupled to a front end and a rear end of hanging part 18 at SLG coupling parts 34. At the time of wearing, SLG 28 assumes a state in which it stands up from the absorbent article body (see FIG. 1(C)).

Inside front part pocket 24 and rear part pocket 26, the lower end part of hanging part 18 of FLG 14 is coupled to surface 12s of absorber 12. In the present invention, the lower end part of the hanging part of the FLG and the leg part of the SLG may not need to be coupled to each other; however, when they are coupled to each other, the behaviors of the FLG and the SLG coordinate with each other.

As shown in FIG. 2, at the time of wearing, hanging part 18 of FLG 14 of absorbent article 100 according to the present invention floats from surface 12s (not shown) of absorber 12 in the crotch part and SLG 28 stands up outward thereof from surface 12s (not shown) of absorber 12, and both line up with respect to each other.

Absorbent article 100 according to the present invention is further provided with waist gathers 38 in the vicinity of the front end and the vicinity of the rear end of leak preventer 10.

Waist gather 38 serves as a fixing band that connects the front end part of the body of absorbent article 100 to the rear end part thereof, attaches the diaper closely around the waist and prevents the absorbent article from sliding down. Waist gather 38 is formed by covering a stretchable member (for example, a polyurethane filament) with a non-woven fabric.

In the present invention, the configuration of the waist gather is not particularly limited and, for example, a publicly-known conventional waist gather may be used. Specifically, examples of such configuration include a configuration in which it is formed by covering a stretchable member (for example, a polyurethane filament) with a non-woven fabric, as in absorbent article 100, and a configuration in which it is formed by folding back the front end part and the rear end part of the external covering sheet, on the upper side, so as to cover the stretchable member (for example, a polyurethane filament).

Absorbent article 100 according to the present invention receives urine and feces, in a stable manner, through an opening formed by a gap between head parts of FLGs 14. Both urine and feces are guided by hanging parts 18 hanging down from head parts 16 of the floating FLGs 14 and reach surface 12s of absorber 12.

The urine received in absorbent article 100 transfers and spreads from front to back and from side to side over surface 12s of absorber 12 and is absorbed across absorber 12. Needless to say, the spreading state on absorber 12 differs depending on the body position of the wearer; however, even when the urine transfers in a largely disproportionate manner to any of the front, rear, right or left, leakage can still be prevented since the urine is captured by wide and deep front part pocket 24 and rear part pocket 26, which are respectively provided in the front part and the rear part of the body absorbent article 100.

In addition, the feces received in absorbent article 100 are enveloped above surface 12s of absorber 12 in rear body R. In some cases, the feces may also be enveloped by wide and deep rear part pocket 26. In addition, when absorbent article 100 includes a pair of right and left SLGs 28, the feces are enveloped in a stable manner in the space formed by surface 12s of absorber 12 and the standing pair of right and left SLGs 28 in rear body R.

Since FLGs 14 of absorbent article 100 according to the present invention are spaced apart from absorber 12 at the time of wearing, a feeling of restraint at the time of wearing is reduced and contact of the urine or feces excreted onto absorber 12 with the wearer's skin is effectively suppressed and thus, the occurrence of hot and stuffy state and rashes is suppressed.

Figure 3:
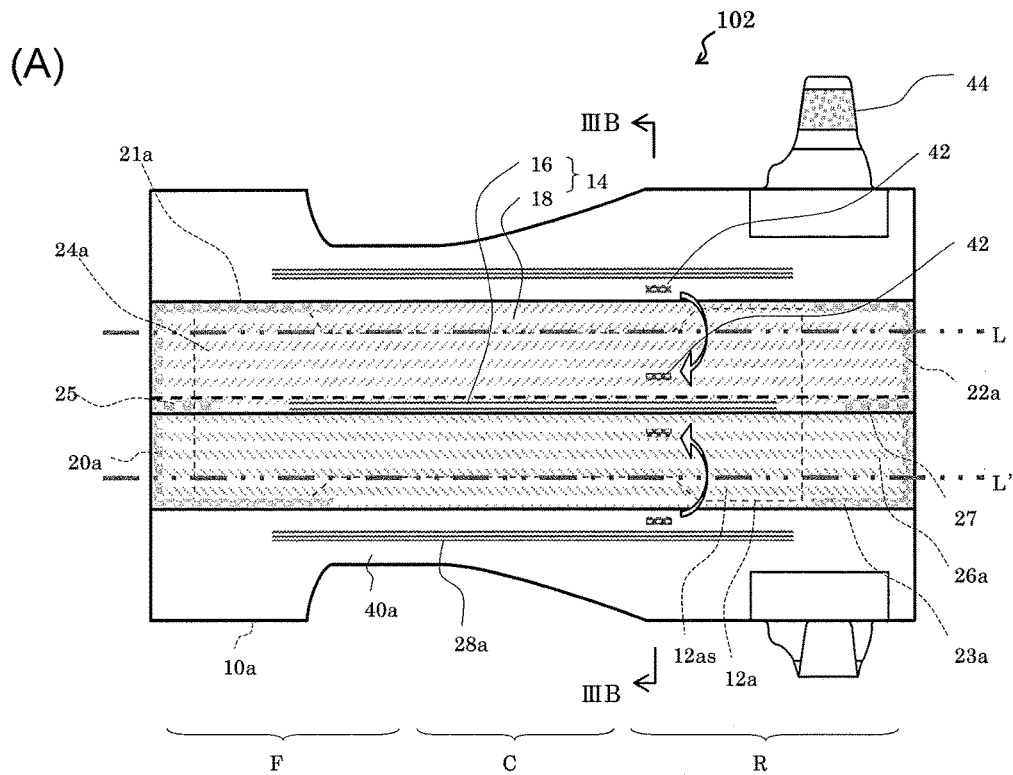
Figure 3:
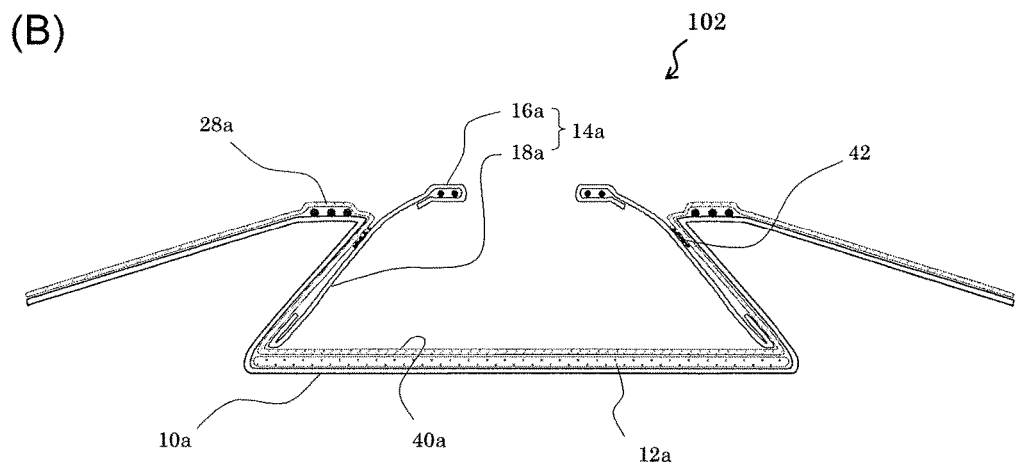

FIG. 3 contains schematic diagrams illustrating an embodiment of the absorbent article according to the present invention. FIG. 3(A) is a developed plan view schematically illustrating the state in which stress is applied to the absorbent article, which is in the form of a tape-type diaper, such that it is pulled in the front-rear direction and the lateral direction to be developed into a substantially planar form. FIG. 3(B) is a lateral end view along line IIIB-IIIB in FIG. 3(A) in a state in which the absorbent article is folded on the inward side along two-dot chain lines L, L' in FIG. 3(A), in which the hanging parts of the FLGs and the leg parts of the SLGs are coupled to each other, and in which no stress is applied thereto.

Absorbent article 102 according to the present invention shown in FIG. 3 is configured as a tape-type diaper; however, it is basically similar to absorbent article 100, which is configured as an underpants-type diaper.

However, absorbent article 102 differs from absorbent article 100 with respect to the point that an external covering sheet is not provided on the underside of leak preventer 10a.

Leak preventer 10a is not particularly limited, and, for example, a sheet-form leak preventer made of an air-permeable PE film/PP spun-bonded composite material may be used.

Top sheet 40a is not particularly limited, and, for example, a PE/PP air-through non-woven fabric may be used.

The size of absorbent article 102 is not particularly limited, and, when it is intended for a medium-sized diaper for infants (approximately 6 kg or more in body weight), the length in the front-rear direction may be, for example, approximately 440 mm, the width in the lateral direction may be approximately 270 mm, and the weight may be approximately 34 g.

In a plan view, absorber 12a is formed in the shape of a sandglass. The width in the lateral direction of the parts of the front body and the rear body where the width is large is approximately 120 mm, the width of the part around the crotch part where the width is small is approximately 90 mm, and the length in the front-rear direction is approximately 350 mm. Absorber 12a is configured by covering 25 g of pulverized pulp and 6 g of SAP with tissue paper. Absorber 12a is arranged above leak preventer 10a and is enveloped between leak preventer 10a and top sheet 40a.

In absorbent article 102, a pair of right and left FLGs 14a are provided, which are arranged, above absorber 12a, from a front end part of the absorbent article body to a rear end part thereof in the length direction, via front body F, crotch part C and rear body R.

FLG 14a includes head part 16a and hanging part 18a that connects to head part 16a.

Head parts 16a of the pair of right and left FLGs 14a are arranged to face inward and hanging parts 18a thereof are arranged to face outward.

As shown in FIG. 3(A), head parts 16a of the pair of right and left FLGs 14a are arranged such that they overlap with each other in the vicinity of the center part in the lateral direction. In this way, it is one of the preferred forms of the present invention to arrange the head parts of the pair of right and left FLGs such that that they overlap with each other, in the vicinity of the center part in the lateral direction, at least partially in the front-rear direction. In particular, a form in which parts of the head parts of the pair of right and left FLGs that overlap with each other in the vicinity of the center part in the lateral direction are present, at least, from the front end part of the absorbent article body to the front body thereof and a form in which parts of the head parts of the pair of right and left FLGs that overlap with each other in the vicinity of the center part in the lateral direction are present, at least, from the rear end part of the absorbent article body to the rear body thereof, are preferable.

Head parts 16a of the pair of right and left FLGs 14a are coupled to each other at parts of the parts where they are overlapped with each other in the vicinity of the center part in the lateral direction. More specifically, head parts 16a of the pair of right and left FLGs 14a are coupled to each other at head part coupling part 25 in the vicinity of the front end and head part coupling part 27 in the vicinity of the rear end. In this way, in the vicinity of the front end and the rear end, hanging parts 18a of the pair of right and left FLGs 14a are in a connected state via head parts 16a. The coupling method is not particularly limited and, for example, the coupling method may be achieved by means of an adhesive.

Head part 16a of FLG 14a is configured by covering two parallel polyurethane filaments (stretchable members) with an SMS non-woven fabric made of PP (for example, having a basis weight of 15 g/m$^2$ and manufactured by AVGOL), and the hanging part of such SMS non-woven fabric configures hanging part 18a. The width of head part 16a is approximately 10 mm and the width of hanging part 18a is approximately 60 mm.

A front end part and a rear end part of FLG 14a are respectively coupled to in the vicinity of a front end part and in the vicinity of a rear end part of the absorbent article body. Specifically, the front end part and the rear end part of FLG 14a (i.e. the parts in FIG. 3(A) where the polyurethane filaments are not present) respectively couples to leak preventer 10a, via top sheet 40a, at front end coupling part 20a and rear end coupling part 22a. In addition, a front end part of hanging part 18a of FLG 14a couples to surface 12as of absorber 12a at front end coupling part 21a. Further, a rear end part of hanging part 18a of FLG 14a couples to leak preventer 10a, via top sheet 40a, at rear end coupling part 23a.

In this way, hanging part 18a is configured to hang down from head part 16a toward surface 12as of absorber 12a in the area from front body F to rear body R (see FIG. 3(B)). The length in the front-rear direction of front end coupling part 21a and rear end coupling part 23a is relatively longer than that of front end coupling part 20a and rear end coupling part 22a. The coupling method is not particularly limited and, for example, the coupling method may be achieved by means of an adhesive.

Hanging parts 18a connect to head parts 16a which oppose each other in the vicinity of the center part in the lateral direction and hang down toward the right and left edge parts (see FIG. 3(B)).

As described above, the front end parts of the pair of right and left FLGs 14a couple to leak preventer 10a, via top sheet 40a, at front end coupling parts 20a, and the pair of right and left FLGs 14a couple to surface 12as of absorber 12a at front end coupling parts 21 in the vicinity of the lower end parts of hanging parts 18a from the front end part to front body F in the front-rear direction. In addition, head parts 16a of the pair of right and left FLG 14a are coupled to each other in the vicinity of the front ends thereof. In this way, front part pocket 24a is formed.

Further, as described above, the rear end parts of the pair of right and left FLGs 14a couple to leak preventer 10a, via top sheet 40a, at rear end coupling parts 22a, and the pair of right and left FLGs 14a couple to leak preventer 10a, via top sheet 40a, at rear end coupling parts 23 in the vicinity of the lower end parts of hanging parts 18a from rear end part to rear body R in the front-rear direction. In addition, head parts 16a of the pair of right and left FLGs 14a are coupled to each other in the vicinity of the rear ends thereof. In this way, rear part pocket 26a is formed.

FLG 14a is spaced apart from surface 12as of absorber 12a in the vicinity of the crotch part.

Absorbent article 102 is provided with two types of leg gathers. More specifically, in addition to the above-described FLGs 14a, SLGs 28 are also provided, which are present in the side edge parts of the absorbent article body. SLG 28 is formed by three parallel polyurethane filaments (stretchable members) being arranged between leak preventer 10a and top sheet 40.

Absorbent article 102 is folded on the inward side, as illustrated by arrows along two-dot chain lines L, L' in FIG. 3(A), and hanging parts 18a of FLGs 14a and the leg parts (the parts of both leak preventer 10a and top sheet 40a which are present on the inward side of the stretchable members configuring SLG 28a) of SLG 28a are joined to each other at joining points 42 present in rear body R shown in FIG. 3(A) (the joining points are shown as being separated in FIG. 3(A)). The joining method is not particularly limited, and, for example, the joining method may be achieved by means of an adhesive (for example, a hot-melt adhesive). The position of joining point 42 in the front-rear direction is approximately 150 mm from the rear end of the absorbent article body.

SLG 28a stands upward due to being joined to FLGs 14a.

On the other hand, head parts 16a of FLGs 14a are coupled to each other at head part coupling part 25 in the vicinity of the front end and at head part coupling part 27 in the vicinity of the rear end; however, they do not couple to each other between head part coupling part 25 and head part coupling part 27. Accordingly, due to contraction of the stretchable members of head parts 16a, a gap which constitutes an opening is formed between the pair of right and left head parts 16a. In addition, since hanging parts 18a of FLGs 14a join SLGs 28a in rear body R, hanging parts 18a of FLGs 14a extend further to both sides. As a result, head parts 16a of FLGs 14a largely extend to both sides as shown in FIG. 3(B) so that the reception of feces is facilitated.

The opening created between the pair of right and left head parts 16a serves as a reception part (i.e. entrance) for urine and feces.

In order to fully fulfill such service, the size of such opening is preferably such that it is capable of enveloping the wearer's urine and feces excretory organs. In absorbent article 102, the clearance (i.e. the width of the opening) between the pair of right and left head parts 16a is at a maximum in the vicinity of joining points 42 in rear body R and narrows down from this point toward the front side, i.e. toward crotch part C and front body F and also narrows down as it approaches the rear end part.

The width of the opening is determined by: the distance between the joining point and the head part of the FLG (or the height from the surface of the absorber to the joining point); the distance between the joining point and the rear end of the absorbent article body; and the stretching force of the stretchable member used in the head part of the FLG.

Means for making the width of the opening fall within an appropriate range are not particularly limited; however, as in absorbent article 102, a form in which the hanging part of the FLG and the leg part of the SLG are coupled is one of the preferred forms of means for extending the clearance between the pair of right and left head parts 16a to both sides.

The position where the hanging part of the FLG and the leg part of the SLG are coupled is not particularly limited; however, it is preferably present from the crotch part and over the rear body and it is more probably present in the vicinity of the crotch part.

Absorbent article 102 receives urine excreted from the wearer's excretory organ in a stable manner through the gap (i.e. opening) between the head parts 16a of the pair of right and left FLGs 14a. Subsequently, the urine is guided by hanging parts 18a that hang down from head parts 16a of FLGs 14a and float thereat so as to be led to surface 12as of absorber 12a.

The urine led to surface 12as of absorber 12a transfers and spreads from front to back and from side to side over surface 12as of absorber 12a and is absorbed across absorber 12a. Needless to say, the spreading state on absorber 12a differs depending on the body position of the wearer; however, even when the urine transfers in a largely disproportionate manner to any of the front, rear, right or left, leakage can still be avoided since the urine is captured by wide and deep front part pocket 24a and rear part pocket 26a which are provided in the front and the rear.

In addition, the feces excreted from the wearer's excretory organ are received in a stable manner through the gap (i.e. opening) between head parts 16a of the pair of right and left FLG 14a. Subsequently, the feces are guided by hanging parts 18a that hang down from head parts 16a of FLGs 14a and float thereat so as to be led to surface 12as of absorber 12a. The feces are enveloped in a stable manner in the space formed by the standing SLGs provided in rear body R and in wide and deep rear part pocket 26a.

The present invention is not limited to the configuration above and, for example, various publicly-known conventional members may also be provided.

In addition to the above-described members, absorbent article 102 is provided with various members, which will be described below.

Detachable members 44 are provided on both the right and left sides of leak preventer 10a in the vicinity of the rear end thereof. On the under surface of leak preventer 10a in the vicinity of the front end thereof, detachable members (not shown) are provided such that they can be detached from detachable members 44. These detachable members may be configured by, for example, various hook-and-loop fasteners. In particular, as for detachable members 44 provided on both the right and left sides of leak preventer 10a in the vicinity of the rear end thereof, Velcro tapes (male) may be used. As for the detachable members provided on the under surface of leak preventer 10a in the vicinity of the front end, TLZs (female) may be used.

Although hanging parts 18a of the pair of right and left FLGs 14a are not coupled to each other in absorbent article 102, it is one of the preferred forms of the present invention to have the hanging parts of the pair of right and lefts FLG connected to each other in the vicinity of the lower end parts thereof in the vicinity of the crotch part so that a transferring passage for the bodily fluids is formed on the inner surface sides of the hanging parts.

In this case, the hanging parts of the pair of right and left FLGs may be connected to each other by being directly coupled to each other.

In addition, the hanging parts of the pair of right and left FLGs may be connected to each other by being respectively coupled to a hanging part support sheet in the vicinity of the lower end parts thereof, and a transferring passage for bodily fluids may be formed by the hanging parts and the hanging part support sheet.

Of these, a form that makes use of a hanging part support sheet is preferable. When the hanging part support sheet is used, since the sectional area of the cross section of the transferring passage for bodily fluids increases, the allowed flow rate also increases and thus, urine is unlikely to overflow from the transferring passage for the bodily fluids. In addition, the manufacture thereof is also simple. More specifically, a hanging part support sheet is arranged, in advance, over the surface of the absorber so as to transverse the hanging parts in the lateral direction; the FLGs are overlaid thereon; the hanging parts of the FLGs and the hanging support sheet are joined to each other at the parts where they overlap with each other; and the hanging parts of the pair of right and left hanging parts are connected to each other by means of the hanging part support sheet and thus, the transferring passage for bodily fluids is formed.

Width W of the hanging part support sheet is set such that the hanging parts of the pair of right and left FLGs, which are arranged to face outward, can be connected to each other in the vicinity of the lower end parts thereof.

For example, when a hanging part support sheet is provided to absorbent article 102 shown in FIG. 3, the width preferably assumes a value between approximately 20 mm longer (i.e. approximately 150 mm) and approximately 20 mm shorter (i.e. approximately 110 mm) relative to the width (approximately 130 mm) between the lower ends of hanging parts 18a of FLGs 14a. Within such range, the cross section of the transferring passage for bodily fluids becomes sufficiently large and no part of the hanging part support sheet is wasted.

Length L of the hanging part support sheet may be set, as needed, according to the length of the parts of the hanging parts of the FLGs which float from the absorber.

It is preferred that the hanging part support sheet is connected to the pair of right and left hanging parts to form the transferring passage for bodily fluids with the hanging parts forming the right and left side surfaces and the hanging part support sheet forming the bottom surface, and thus urine does not leak from the transferring passage for bodily fluids. Accordingly, a hydrophobic material having a leak prevention property is preferred as the material of the hanging part support sheet. Examples thereof include a PP or PE-based spun-melt non-woven fabric and a soft synthetic resin film made of PE, PP, EVA, polyurethane, etc. and the like.

On the other hand, it is preferred that the hanging part support sheet is made of a hydrophilic material for achieving a smooth transfer (i.e. fast and uniform transfer) of urine.

In view of the points above, it is one of the preferred forms to make the hanging part support sheet from a composite material in which a hydrophobic material and a hydrophilic material are combined.

Examples of compounding methods for combining a hydrophobic material and a hydrophilic material include lamination, coating, and binding together using an adhesive.

Examples of compound hanging part support sheets in which a hydrophobic material and a hydrophilic material are combined include a hanging part support sheet in which an SMS non-woven fabric made of PP and a PE film are bound together, a laminate of tissue and a PE film and a laminate of a rayon non-woven fabric and an EVA film.

The entirety or alternatively only a part thereof, of the hanging part support sheet in the front-rear direction and in the lateral direction may be compounded with a hydrophobic material and a hydrophilic material.

Figure 4:
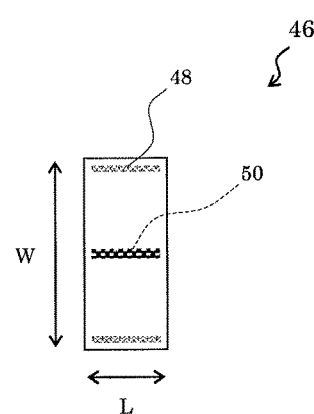
Figure 4:
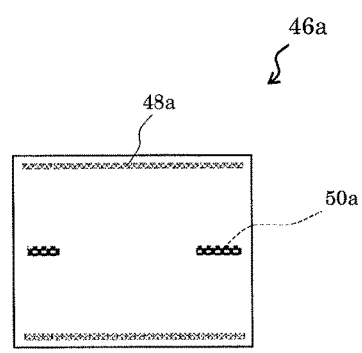
Figure 4:
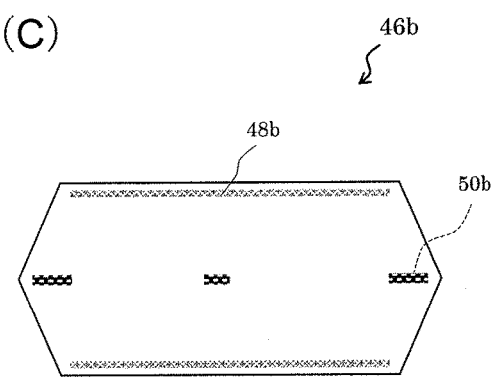
Figure 4:
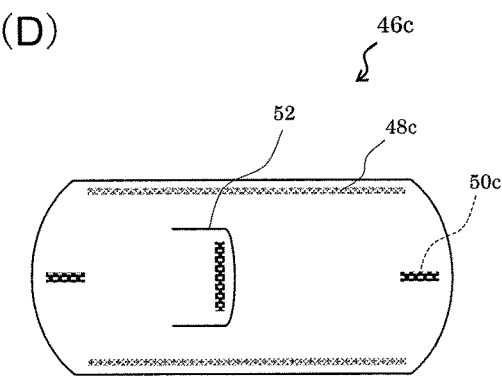
Figure 4:
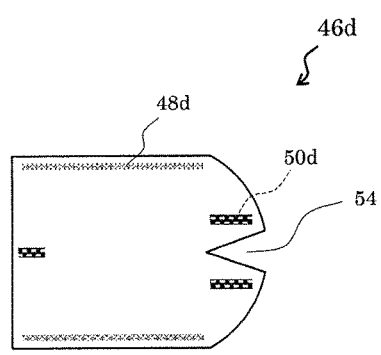
Figure 4:
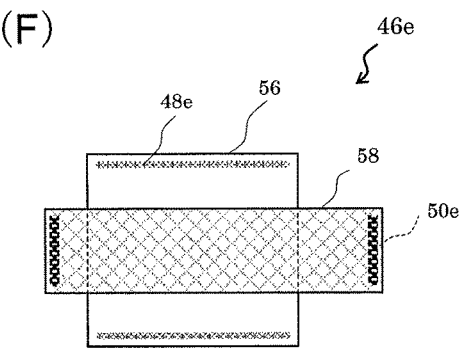

FIG. 4 contains schematic plan views illustrating various hanging part support sheets. In the description below, the size of the hanging part support sheet has a numerical value intended for a medium-sized diaper for infants (approximately 6 kg or more in body weight); however, the present invention is not limited thereto.

Hanging part support sheet 46 shown in FIG. 4(A) is rectangular, with length "L" in the front-rear direction being shorter than width "W" in the lateral direction. The length in the front-rear direction is approximately 20 to 150 mm.

Hanging part support sheet 46 includes: coupling parts 48 for coupling to the hanging parts, which extend over substantially the entire length in the front-rear direction in the vicinity of the right and left edge parts; and coupling part 50 for coupling to the surface of the absorber, which extends over substantially the entire length in the front-rear direction in the vicinity of the center in the lateral direction. In the present invention, as in this case, it is preferred that the hanging part support sheet includes a coupling part for coupling to the surface of the absorber.

Preferably, hanging part support sheet 46 is provided at the crotch part.

Hanging part support sheet 46a shown in FIG. 4(B) is rectangular, with the length in the front-rear direction being longer than the length in the lateral direction. The length in the front-rear direction is approximately 110 to 300 mm.

Hanging part support sheet 46a includes: coupling parts 48a for coupling to the hanging parts, which extend over substantially the entire length in the front-rear direction in the vicinity of the right and left edge parts; and coupling parts 50a for coupling to the surface of the absorber, which are located at two locations including the vicinity of the front end and the vicinity of the rear end, in the vicinity of the center in the lateral direction.

Preferably, hanging part support sheet 46a is provided within the range from the front part pocket to the rear part pocket.

Hanging part support sheet 46b shown in FIG. 4(C) has a deformed rectangular shape, with the length in the front-rear direction being longer than the width in the lateral direction. The length in the front-rear direction is approximately 110 to 300 mm. In particular, an apex is created in the center part of each of the front end and the rear end and thus, the hanging part support sheet assumes a hexagonal shape.

Hanging part support sheet 46b includes: coupling parts 48b for coupling to the hanging parts, which extend over substantially the entire length in the front-rear direction in the vicinity of the right and left edge parts: and coupling parts 50b for coupling to the surface of the absorber, which are located at three locations including the vicinity of the front end, the vicinity of the rear end and the vicinity of the center, in the vicinity of the center in the lateral direction. The number of coupling parts for coupling to the surface of the absorber may be one, two, four or more.

Preferably, hanging part support sheet 46b is provided within the range from the front part pocket to the rear part pocket.

Hanging part support sheet 46c shown in FIG. 4(D) has a deformed rectangular shape, with the length in the front-rear direction being longer than the width in the lateral direction. The length in the front-rear direction is approximately 110 to 300 mm. In particular, the center part in each of the front end and the rear end are convexly curved.

In hanging part support sheet 46c, C-shaped slit 52 is provided in the center part in the front-rear direction and the part surrounded by such slit 52 can bend downward. This bent-down part serves as an exit for the transferring passage for bodily fluids.

Hanging part support sheet 46c includes: coupling parts 48c for coupling to the hanging parts, which extend over substantially the entire length in the front-rear direction in the vicinity of the right and left edge parts: and coupling parts 50c for coupling to the surface of the absorber, which are located at three locations including the vicinity of the front end, the vicinity of the rear end and the part surrounded by slit 52, in the vicinity of the center in the lateral direction.

Preferably, hanging part support sheet 46c is provided within the range from the front part pocket to the rear part pocket.

Hanging part support sheet 46d shown in FIG. 4(E) has a deformed rectangular shape, with the length in the front-rear direction being longer than the width in the lateral direction. The length in the front-rear direction is approximately 110 to 250 mm. In particular, the center part in the rear end is convexly curved and also has notch 54.

Hanging part support sheet 46d includes: coupling parts 48d for coupling to the hanging parts, which extend over substantially the entire length in the front-rear direction in the vicinity of the right and left edge parts: and coupling parts 50d for coupling to the surface of the absorber, which are located at a total of three locations including one location in the vicinity of the front end in the vicinity of the center in the lateral direction and two locations on both sides of notch 54 in the vicinity of the rear end. The vicinity of notch 54 serves as an exit for transferring passage for bodily fluids.

Hanging part support sheet 46e shown in FIG. 4 (F) is a compound sheet in which a rectangular hydrophobic sheet 56 and a rectangular hydrophilic sheet 58 are combined. In particular, hydrophilic sheet 58, with a width in the lateral direction being shorter than that of hydrophobic sheet 56 and a length in the front-rear direction being longer than that of hydrophobic sheet 56, is overlaid on and coupled to the upper side of hydrophobic sheet 56.

The compound sheet in which hydrophobic sheet 56 and hydrophilic sheet 58 are combined is not particularly limited; and examples thereof include a compound sheet in which an SMS non-woven fabric made of PP (manufactured by AVGOL) and tape-shaped TCF (manufactured by Futamura Chemical Co., Ltd.) are partially combined by means of a hot-melt adhesive.

Hanging part support sheet 46e includes: coupling parts 48e for coupling to the hanging parts, which extend over substantially the entire length in the front-rear direction in the vicinity of the right and left edge parts of hydrophobic sheet 56: and coupling parts 50e for coupling to the surface of the absorber, which extend over substantially the entire width in the lateral direction in the vicinity of the front and rear end parts of hydrophilic sheet 58.

Figure 5:
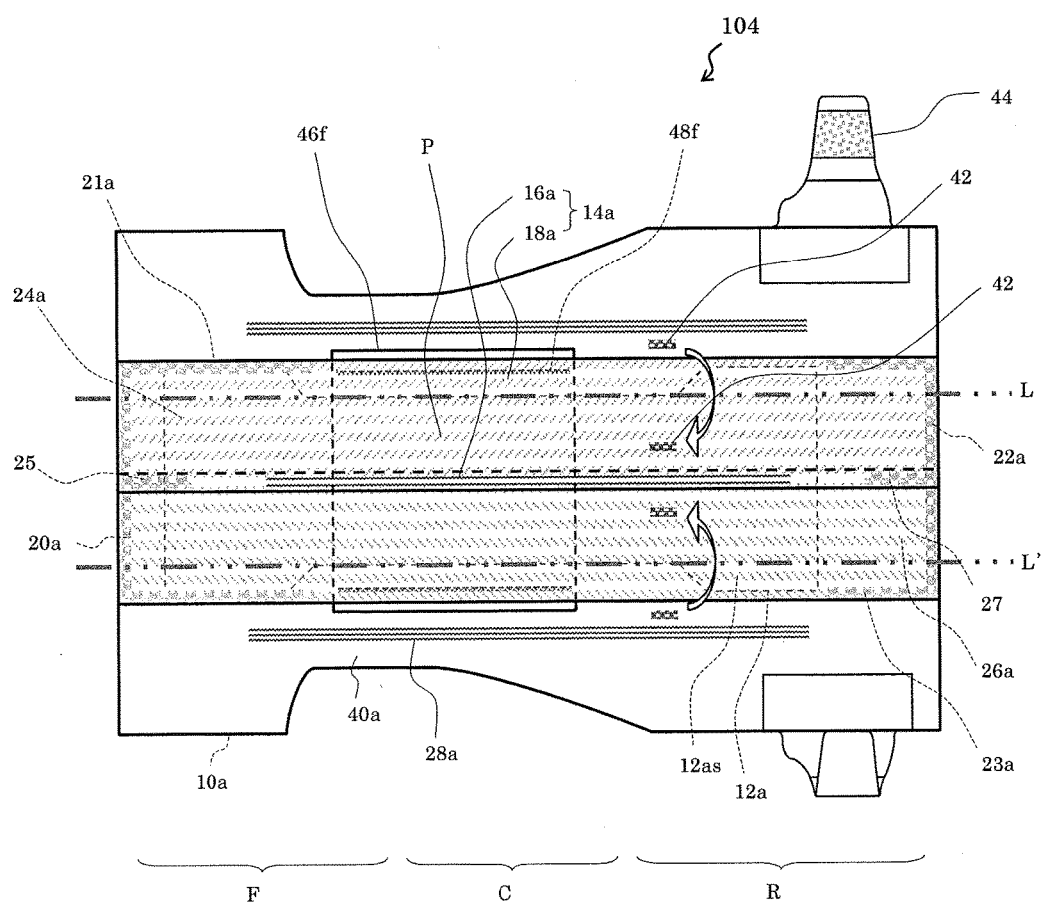
FIG. 5 is a schematic developed plan view illustrating another embodiment of the absorbent article according to the present invention.
Figure 6:
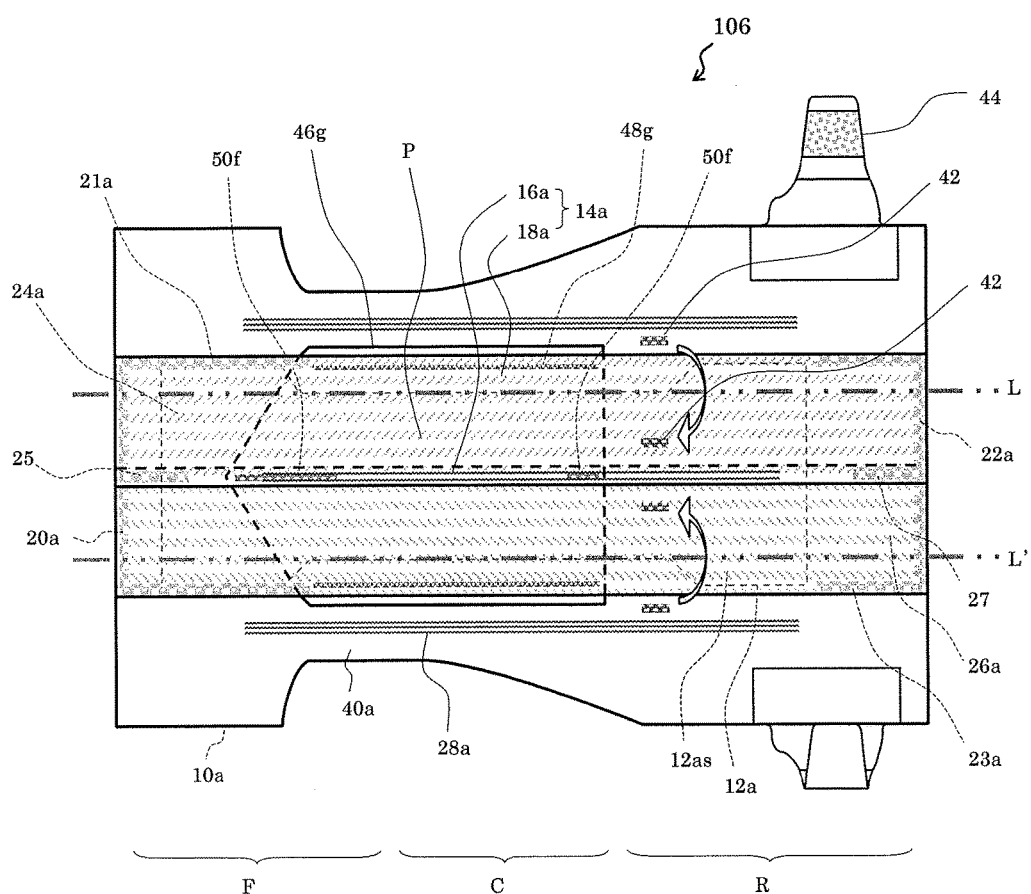
FIG. 6 is a schematic developed plan view illustrating a further embodiment of the absorbent article according to the present invention.

Each absorbent article shown in FIGS. 5 to 7 is basically similar to the absorbent article shown in FIG. 3; however, by combining various hanging part support sheets, such as those shown in FIG. 4, each represents an example of the embodiment provided with different and new functions.

FIG. 5 is a schematic developed plan view illustrating another embodiment of an absorbent article according to the present invention. FIG. 5 shows the state in which stress is applied to the absorbent article, which is in the form of a tape-type diaper, such that it is pulled in the front-rear direction and the lateral direction to be developed into a substantially planar form.

Absorbent article 104 shown in FIG. 5 is basically similar to absorbent article 102 shown in FIG. 3; however, it differs therefrom with respect to the point that it includes hanging part support sheet 46f.

Hanging part support sheet 46f is rectangular, with the length (approximately 130 mm) in the front-rear direction being slightly shorter than the width (approximately 140 mm) in the lateral direction.

Hanging part support sheet 46f is arranged over most of crotch part C and part of front body F.

For example, for hanging part support sheet 46f, a laminate sheet (manufactured by Futamura Chemical Co., Ltd.) having a hydrophobic sheet (for example, a PE film of approximately 10 μm) on the underside thereof and a hydrophilic sheet (for example, TCF having a basis weight of 25 g/m²) on the upper side thereof may be used.

Hanging parts 18a of the pair of right and left FLGs 14a are connected to each other by being respectively coupled to hanging part support sheet 46f at coupling parts 48f in the vicinity of the lower end parts thereof in the vicinity of crotch part C, and transferring passage P for bodily fluids is formed by means of hanging parts 18a and hanging part support sheet 46f. The right and left side surfaces of transferring passage P for bodily fluids are formed by means of hanging parts 18a and the bottom surface thereof is formed by means of hanging part support sheet 46f.

Transferring passage P for bodily fluids extends from crotch part C to front body F.

When no stress is applied to absorbent article 104 shown in FIG. 5 and such absorbent article is in a relaxed state, the stretchable members configuring head parts 16a of the pair of right and left FLGs 14a contract and thus, an opening is formed.

In this way, transferring passage P for bodily fluids, which is a large space having a width of approximately 130 mm and a depth of approximately 50 mm, and which opens upwardly, is formed from crotch part C to front body F.

Transferring passage P for bodily fluids floats from surface 12as of absorber 12a and is kept spaced apart from surface 12as of absorber 12a.

Substantially the total volume of the urine excreted from the wearer is received through the opening into transferring passage P for bodily fluids. The flow rate of the urine received in transferring passage P for bodily fluids is significantly reduced and such urine is supplied, in an equalized state, onto surface 12as of absorber 12a in front body F from the front of transferring passage P for bodily fluids and is also supplied onto surface 12as of absorber 12a in rear body R from the rear of transferring passage P for bodily fluids. The urine is absorbed by making use of the entire absorber 12a while being spread from front to back and from side to side over surface 12as of absorber 12a.

Needless to say, the proportion of the urine amount transferring to the front side and the rear side from transferring passage P for bodily fluids differs depending on the wearer's body position; however, even when the urine transfers in a largely disproportionate manner to either the front or the rear, leakage can still be avoided since the urine is captured by wide and deep front part pocket 24a and rear part pocket 26 which are respectively provided in the front and the rear.

FIG. 6 is a schematic developed plan view illustrating a further embodiment of an absorbent article according to the present invention. FIG. 6 shows the state in which stress is applied to the absorbent article, which is in the form of a tape-type diaper, such that it is pulled in the front-rear direction and the lateral direction to be developed into a substantially planar form.

Absorbent article 106 shown in FIG. 6 is basically similar to absorbent article 102 shown in FIG. 3; however, it differs therefrom with respect to the point that it includes hanging part support sheet 46g.

Hanging part support sheet 46g has a deformed rectangular shape, and in particular, it has an apex in the center part of the front end and assumes a pentagonal shape. The length (approximately 200 mm (at the center part with the longest length)) of hanging part support sheet 46g in the front-rear direction is longer than the width (approximately 140 mm) thereof in the lateral direction.

Hanging part support sheet 46g is arranged from crotch part C to front body F. For example, for hanging part support sheet 46g, a laminate sheet (manufactured by Futamura Chemical Co., Ltd.) having a hydrophobic sheet (for example, a PE film of approximately 10 µm) on the underside thereof and a hydrophilic sheet (for example, TCF having a basis weight of 25 g/m$^2$) on the upper side thereof may be used.

Hanging parts 18a of the pair of right and left FLGs 14a are connected to each other by being respectively coupled to hanging part support sheet 46g at coupling parts 48g in the vicinity of the lower end parts thereof in the vicinity of crotch part C, and transferring passage P for bodily fluids is formed by means of hanging parts 18a and hanging part support sheet 46g. The right and left side surfaces of transferring passage P for bodily fluids are formed by means of hanging parts 18a and the bottom surface thereof is formed by means of hanging part support sheet 46g.

Transferring passage P for bodily fluids extends from crotch part C to front body F and connects to front part pocket 24a by the front end of hanging part support sheet 46g entering into the inside of front part pocket 24a.

Hanging part support sheet 46g couples to surface 12as of absorber 12a at two coupling parts 50f in the vicinity of the front end and the vicinity of the rear end, in the vicinity of the center in the lateral direction.

When no stress is applied to absorbent article 106 shown in FIG. 6 and such absorbent article is in a relaxed state, the stretchable members configuring head parts 16a of the pair of right and left FLGs 14a contract and thus, an opening is formed.

In this way, transferring passage P for bodily fluids, which is a large space having a width of approximately 130 mm and a depth of approximately 50 mm, and which opens upwardly, is formed so as to extend from crotch part C to front body F and to connect to front part pocket 24a.

While transferring passage P for bodily fluids couples to surface 12as of absorber 12a at two coupling parts 50f, which correspond to the front end and the rear end of transferring passage P for bodily fluids, it floats from surface 12as of absorber 12a in parts other than the two coupling parts above and is kept spaced apart from surface 12as of absorber 12a. The position of the bottom surface of transferring passage P for bodily fluids is basically low at the exit at the rear end of crotch part C and becomes higher toward front body F. However, in the vicinity of the apex at the front end center part, such position is lowered by means of coupling part 50f for coupling to surface 12as of absorber 12a so as to easily lead the urine into front part pocket 24a.

Substantially the total volume of the urine excreted from the wearer is received through the opening into transferring passage P for bodily fluids. The flow rate of the urine received in transferring passage P for bodily fluids is significantly reduced and such urine is supplied, in an equalized state, onto surface 12as of absorber 12a in front body F from the front of transferring passage P for bodily fluids and is also supplied onto surface 12as of absorber 12a in rear body R from the rear of transferring passage P for bodily fluids. The urine is absorbed by making use of the entire absorber 12a while being spread from front to back and from side to side over surface 12as of absorber 12a.

Here, when the urine transfers from transferring passage P for bodily fluids onto surface 12as of absorber 12a, while it is needless to say that it differs depending on the body position, most of the urine transfers from the exit at the rear end onto surface 12as of absorber 12a and a portion thereof transfers from the exist at the front end into front part pocket 24a.

The urine transferred forward in transferring passage P for bodily fluids passes through the vicinity of the apex of the front end of hanging part support sheet 46g and is selectively supplied from the center part inside front part pocket 24a onto surface 12as of absorber 12a. From there, the urine first spreads over the entire front part pocket 24a by flowing over surface 12as of absorber 12a. In addition, the unabsorbed urine passes under hanging part support sheet 46g and transfers to the absorber 12a, which is on the rear side with respect to front part pocket 24a, by gradually penetrating therein.

On the other hand, the urine transferred rearward in transferring passage P for bodily fluids passes through the vicinity of the center part of the rear end and is selectively supplied onto surface 12as of absorber 12a. From there, the urine spreads from front to back and from side to side. The amount of urine that transfers to the sides is significantly reduced as compared to the amount that transfers to the front and back; however, even when the urine transfers to the sides, the pair of right and left SLGs 28a arranged outward of the pair of right and left FLGs 14a prevent side leakage. In addition, even when a large amount of urine spreads to the rear side, rear part pocket 26a prevent leakage.

Since transferring passage P for bodily fluids is formed with a slope such as that described above, almost no urine that is excreted stays within transferring passage P for bodily fluids. In addition, since surface 12as of absorber 12a, except for the opening, is covered with hanging parts 18a of FLGs 14a, the possibility of the wearer's skin making contact with urine is extremely small.

The same applies to the situation when the excreted amount of urine exceeds the absorption capacity of absorber 12a and the urine oozes out onto top sheet 40a, since hanging part support sheet 46g has a leak prevention property and surface 12as of absorber 12a is not in contact with the wearer's skin.

FIG. 7 contains schematic developed plan views illustrating a further embodiment of an absorbent article according to the present invention. FIG. 7(A) shows the state in which stress is applied to the absorbent article, which is in the form of a tape-type diaper, such that it is pulled in the front-rear direction and the lateral direction to be developed into a substantially planar form. FIG. 7(B) is a longitudinal sectional view along line VIIB-VIIB in FIG. 7(A) in a state in which the absorbent article is folded on the inward side along two-dot chain lines L, L' in FIG. 7(A), in which the hanging parts of the FLGs and the leg parts of the SLGs are coupled to each other, and in which no stress is applied thereto.

Absorbent article 108 shown in FIG. 7 is basically similar to absorbent article 102 shown in FIG. 3; however, it differs therefrom with respect to the point that it includes hanging part support sheet 46h.

Hanging part support sheet 46h has a deformed rectangular shape, and in particular, the center part in the front end is convexly curved. The length (approximately 310 mm (at the center part with the longest length)) of hanging part support sheet 46h in the front-rear direction is longer than the width (approximately 140 mm) thereof in the lateral direction.

In hanging part support sheet 46h, arc-shaped slit 52a is provided in the vicinity of the center, in the center part in the front-rear direction, and the part surrounded by such slit 52a can bend downward. This bent-down part serves as an exit for transferring passage P for bodily fluids.

Hanging part support sheet 46h is arranged over the entire crotch part C, part of front body F and part of rear body R.

For example, for hanging part support sheet 46h, a laminate sheet (manufactured by Futamura Chemical Co., Ltd.) having a hydrophobic sheet (for example, a PE film of approximately 10 μm) on the underside thereof and a hydrophilic sheet (for example, TCF having a basis weight of 25 g/m$^2$) on the upper side thereof may be used.

Hanging parts 18a of the pair of right and left FLGs 14a are connected to each other by being respectively coupled to hanging part support sheet 46h at coupling parts 48h in the vicinity of the lower end parts thereof in the vicinity of crotch part C, and transferring passage P for bodily fluids is formed by means of hanging parts 18a and hanging part support sheet 46h. The right and left side surfaces of transferring passage P for bodily fluids are formed by means of hanging parts 18a and the bottom surface thereof is formed by means of hanging part support sheet 46h.

Transferring passage P for bodily fluids extends from crotch part C to each of front body F and rear body R and connects to front part pocket 24a and to rear part pocket 26a by the front end and rear end of hanging part support sheet 46h respectively entering into the inside of front part pocket 24a and rear part pocket 26a.

Hanging part support sheet 46h couples to surface 12as of absorber 12a at two coupling parts 50g in the vicinity of the front end and the vicinity of the rear end, in the vicinity of the center in the lateral direction, and at coupling part 50g which constitutes the part surrounded by slit 52a and bends down to the underside.

When no stress is applied to absorbent article 108 shown in FIG. 7 and such absorbent article is in a relaxed state, the stretchable members configuring head parts 16a of the pair of right and left FLGs 14a contract and thus, an opening is formed.

In this way, transferring passage P for bodily fluids, which is a large space having a width of approximately 130 mm and a depth of approximately 50 mm, and which opens upwardly, is formed so as to extend from crotch part C to each of front body F and rear body R and to respectively connect to front part pocket 24a and rear part pocket 26a.

While transferring passage P for bodily fluids couples to surface 12as of absorber 12a at three coupling parts 50g of transferring passage P for bodily fluids, it floats from surface 12as of absorber 12a in parts other than the coupling parts above and is kept spaced apart from surface 12as of absorber 12a. Accordingly, while it is needless to say that it differs depending on the body position, the bottom surface of transferring passage P for bodily fluids is formed with a slope in which the position thereof is high in front body F and rear body R, lowers down toward crotch part C, is further lowered at the exit of coupling part 50g, which constitutes the part surrounded by slit 52a and bends down to the underside.

Substantially the total volume of the urine excreted from the wearer is received through the opening into transferring passage P for bodily fluids. The flow rate of the urine received in transferring passage P for bodily fluids is significantly reduced and such urine is supplied, in an equalized state, onto surface 12as of absorber 12a in front body F from the front of transferring passage P for bodily fluids, is supplied onto surface 12as of absorber 12a in rear body R from the rear of transferring passage P for bodily fluids, and is supplied onto surface 12as of absorber 12a in crotch part C from the exit that is formed by slit 52a and bends down to the underside in the center part of transferring passage P for bodily fluids. The urine is absorbed by making use of the entire absorber 12a while being spread from front to back and from side to side over surface 12as of absorber 12a.

Here, when the urine transfers from transferring passage P for bodily fluids onto surface 12as of absorber 12a, most of the urine flows out from the vicinity of the center of the exit formed by slit 52a; however, depending on the body position, a portion thereof also overflows from the exit in the front body and is absorbed in front part pocket 24a. Almost no urine transfers to the part of transferring passage P for bodily fluids in rear body R.

The urine transferred forward in transferring passage P for bodily fluids passes through the vicinity of the apex in the front end of hanging part support sheet 46h and is selectively supplied from the center part inside front part pocket 24a onto surface 12as of absorber 12a. From there, the urine first spreads over the entire front part pocket 24a by flowing over surface 12as of absorber 12a. In addition, the unabsorbed urine passes under hanging part support sheet 46h and transfers to the absorber 12a which is on the rear side with respect to front part pocket 24a by gradually penetrating therein.

Most of the urine is selectively supplied mainly from the center part in the lateral direction of the exit formed by slit 52a onto surface 12as of absorber 12a. From there, the urine transfers and spreads from front to back and from side to side. The amount of urine that spreads to the sides is significantly reduced as compared to the case of a regular diaper; however, even when the urine transfers to the sides, the pair of right and left SLGs 28a arranged outward of the pair of right and left FLGs 14a prevent side leakage. In addition, even when a large amount of urine spreads to the rear side, rear part pocket 26a prevent leakage.

Since transferring passage P for bodily fluids is formed with a slope such that as described above, almost no urine that is excreted stays within transferring passage P for bodily fluids. In addition, since surface 12as of absorber 12a, except for the opening, is covered with hanging parts 18a of FLGs 14a, the possibility of the wearer's skin making contact with urine is extremely small.

The same applies to the situation when the excreted amount of urine exceeds the absorption capacity of absorber 12a and the urine oozes out onto top sheet 40a, since hanging part support sheet 46h has a leak prevention property and surface 12as of absorber 12a is not in contact with the wearer's skin.

Feces excreted from the wearer and received through the opening of transferring passage P for bodily fluids are enveloped on the rear side with respect to slit 52a of transferring passage P for bodily fluids.

It should be noted that, since a large step difference is present between the rear side with respect to slit 52a and the exit formed by slit 52*a*, the urine is unlikely to transfer rearward from slit 52*a* and thus, an extremely effective separation of urine and feces is achieved.

When the fluidity of feces is small, such feces stay within transferring passage P for bodily fluids.

In contrast, when the fluidity of feces is large, such feces transfer from the exit of transferring passage P for bodily fluids onto surface 12*as* of absorber 12*a*. The feces transferred forward transfer onto surface 12*as* of absorber 12*a* through the exit formed by slit 52*a*, and are enveloped in the space present between surface 12*as* of absorber 12*a* and hanging part support sheet 46*h*, the water thereof being absorbed by absorber 12*a* and thus, the feces being fixed thereat. The feces transferred rearward transfer from the rear end of transferring passage P for bodily fluids onto surface 12*as* of absorber 12*a*, and are enveloped inside rear part pocket 26*a*, the water thereof being absorbed by absorber 12*a* and thus, the feces being fixed thereat.

Accordingly, since the feces that stay within transferring passage P for bodily fluids are only feces which has little fluidity and thus solid and since, except for the opening, hanging parts 18*a* of FLGs 14*a* cover the wearer's skin, the area of the wearer's skin that makes contact with feces is limited to the periphery of the anus. Thus, the risk of rashes is reduced and also cleaning after removal is facilitated. Moreover, when absorbent article 108 according to the present invention is used for a person in need of care, the burden of a care-taker is made extremely small.

The absorbent article according to the present invention effectively suppresses the possibility of the urine and feces excreted on the absorber making contact with the wearer's skin by the head parts of the pair of right and left FLGs being arranged to face inward and the hanging parts thereof being arranged to face outward.

In order to fulfill this function more effectively, in addition to the form in which, for example, as in absorbent article 102 shown in FIG. 3, the head parts of the pair of right and left FLGs are arranged so as to overlap with each other, in the vicinity of the center part in the lateral direction, at least partially in the front-rear direction, a form in which the space between the head parts that oppose each other of the pair of right and left FLGs is covered, with means of a leak prevention sheet, at least partially in the front-rear direction, is also preferred.

In particular, the form in which the part in which the space between the head parts of the pair of right and left FLGs is covered is present at least from the front end part of the absorbent article body to the front body thereof, and the form in which the part in which the space between the head parts of the pair of right and left FLGs is covered is present at least from the rear end part of the absorbent article body to the rear body thereof, are preferred.

FIG. 8 contains schematic plan views illustrating various examples of FLGs in which a space between the opposing head parts is covered with means of a leak prevention sheet, at least partially in the front-rear direction.

FLG 14*b* shown in FIG. 8(A) includes head part 16*b* and hanging part 18*b* that connects to head part 16*b*, wherein head part 16*b* is arranged to face inward and hanging part 18*b* is arranged to face outward. Head parts 16*b* of the pair of right and left FLGs 14*b* oppose each other with clearance d therebetween. A front end part and a rear end part of FLG 14*b* are respectively coupled to in the vicinity of a front end part and in the vicinity of a rear end part of the absorbent article body (not shown), and hanging part 18*b* is configured to hang down from head part 16*b* toward the absorber (not shown).

Front part covering sheet 60 and rear part covering sheet 62 are respectively provided above the pair of right and left FLGs 14*b* in the vicinity of the front end part thereof and the vicinity of the rear end part thereof in such a manner that they stride over and cover such parts. Each of front part covering sheet 60 and rear part covering sheet 62 is a leak prevention sheet and, for example, a hydrophobic non-woven fabric and a laminated body of a non-woven fabric and a film may be used.

The part in which the space between heading parts of the pair of right and left FLGs is covered with means of front part covering sheet 60 may be present from the front end part of the absorbent article body (not shown) to the front body.

In addition, the part in which the space between heading parts of the pair of right and left FLGs is covered with means of rear part covering sheet 62 may be present from the rear end part of the absorbent article body (not shown) to the rear body.

Since neither of front part covering sheet 60 and rear part covering sheet 62 is directly coupled to FLGs 14*b*, FLGs 14*b* have some degree of freedom, to the extent that they can be slightly moved to the sides and to the front and the rear.

It should be noted that the forms of arranging front part covering sheet 60 and rear part covering sheet 62 on the absorbent article body and coupling them thereto will be described hereinafter.

FLGs 14*c* shown in FIG. 8(B) includes head part 16*c* and hanging part 18*c* that connects to head part 16*c*, wherein head part 16*c* is arranged to face inward and hanging part 18*c* is arranged to face outward. Head parts 16*c* of the pair of right and left FLGs 14*c* oppose each other, at center opening Oc, with clearance d therebetween. A front end part and a rear end part of FLG 14*c* are respectively coupled to in the vicinity of a front end part and in the vicinity of a rear end part of the absorbent article body (not shown), and hanging part 18*c* is configured to hang down from head part 16*c* toward the absorber (not shown).

FLGs 14*c* may be obtained using one or two substantially rectangular sheets (for example, non-woven fabrics).

For example, head parts 16*c* of FLGs 14*c* are formed by applying a right and left pair of stretchable materials under tension at the center part in the lateral direction of a sheet such that clearance d is created therebetween, or alternatively, by sandwiching a right and left pair of stretchable materials under tension at the center part in the lateral direction of two sheets such that clearance d is created therebetween.

Subsequently, the section between the pair of right and left stretchable materials is cut out in a rectangular shape with rounded corners so as to form center opening Oc.

Two slits 63 are then provided in each of the right and left edge parts of the sheet(s) and hanging part 18*c* of FLG 14*c* is formed by the section between slits 63. It should be noted that, instead of slit 36, a notch may be provided and the same effect can still be obtained.

In this way, FLG sheet 65 formed with FLGs 14*c* is obtained.

As with FLGs 14*c*, it is one of the preferable forms of the present invention to have the front parts and the rear parts of the pair of FLGs connected to one another.

It should be noted that the forms of arranging FLG sheet 65 on the absorbent article body and coupling it thereto will be described hereinafter.

FLGs 14*d* shown in FIG. 8(C) includes head part 16*d* and hanging part 18*d* that connects to head part 16*d*, wherein head part 16*d* is arranged to face inward and hanging part 18*d* is arranged to face outward. Head parts 16*d* of the pair of right and left FLGs 14*d* oppose each other, at front part opening Of and rear part opening Or, with clearance d therebetween. A front end part and a rear end part of FLG 14*d* are respectively coupled to in the vicinity of a front end part and in the vicinity of a rear end part of the absorbent article body (not shown), and hanging part 18*d* is configured to hang down from head part 16*d* toward the absorber (not shown).

Except for cutting out two sections in a sheet(s) and for leaving a bridge part to remain therebetween in order to form front part opening Of and rear part opening Of, FLG 14*d* can be obtained, in a similar manner to FLG 14*c*, by making use of one or two substantially rectangular sheets (for example, non-woven fabrics).

In this way, FLG sheet 65*a* formed with FLGs 14*d* is obtained.

As with FLGs 14*d*, one of the preferable forms of the present invention to have the front parts, the rear parts and the center part of the pair of FLGs connected to one another.

FIG. 9 contains schematic diagrams illustrating a further example of an absorbent article according to the present invention. FIG. 9(A) illustrates the state in which an absorbent article, in the form of an underpants-type diaper, is cut along the right and left side parts (denoted with "Z" and "Z" in the figure) of the waist gather and in which stress is applied to the absorbent article such that it is pulled in the front-rear direction and the lateral direction to be developed into a substantially planar form. FIG. 9(B) is a lateral end view along line IXB-IXB in FIG. 9(A) in the state described above.

Absorbent article 110 shown in FIG. 9 is basically similar to absorbent article 100 illustrated in FIGS. 1 and 2; however, it differs therefrom with respect to the point that it includes front part covering sheet 60 and rear part covering sheet 62 shown in FIG. 8(A).

Front part covering sheet 60 covers the space between head parts 16 of the pair of right and left FLGs 14 in the vicinity of the front end part thereof. In addition, front part covering sheet 60 covers head parts 16 and hanging parts 18 of the pair of right and left FLGs 14, from above, over the range between the right and left edge parts of absorber 12.

A front end part of front part covering sheet 60 is joined to the front end part of the absorbent article body, along with the front end parts of FLGs 14, by means of coupling parts 66. Similarly to rear part covering sheet 62 shown in FIG. 9(B), the left and right edge parts of front part covering sheet 60 are coupled to surface 12*s* of absorber 12 and are sealed such that no leakage occurs.

Since front part covering sheet 60 is joined along three sides including the front end part and the right and left edge parts described above, front part pocket 24', which is larger and deeper than front part pocket 24, is formed. In this way, leakage is more effectively prevented. Except for the front end part, front part covering sheet 60 is not coupled to FLGs 14. This allows FLGs 14 a greater degree of freedom for deformation.

Rear part covering sheet 62 covers the space between head parts 16 of the pair of right and left FLGs 14 in the vicinity of the rear part thereof. In addition, rear part covering sheet 62 covers head parts 16 and hanging parts 18 of the pair of right and left FLGs 14, from above, over the range between the right and left edge parts of absorber 12.

A rear end part of rear part covering sheet 62 is joined to the rear end part of the absorbent article body, along with the rear end parts of FLGs 14, by means of coupling parts 70. As shown in FIG. 9(B), the left and right edge parts of rear part covering sheet 62 are coupled to surface 12*s* of absorber 12 and are sealed such that no leakage occurs.

Since rear part covering sheet 62 is joined along three sides including the rear end part and the right and left edge parts described above, rear part pocket 26', which is larger and deeper than rear part pocket 26, is formed. In this way, leakage is more effectively prevented.

Except for the rear end part, rear part covering sheet 62 is not coupled to FLGs 14. This allows FLGs 14 a greater degree of freedom for deformation.

SLG 28 that extends outside of absorber 12 is folded back, on the inward side, so as to cover a side edge part of front part covering sheet 60, a side edge part of rear part covering sheet 62 and a lower end part of hanging part 18. A front end part and a rear end part of the head part (the part that includes no stretchable member) of SLG 28 are respectively coupled onto the covering sheets at SLG coupling parts 64 and 68.

In absorbent article 110, the shape and size of front part pocket 24' and rear part pocket 26' are the same; however, the present invention is not limited thereto and the shape and size may be different.

FIG. 10 contains schematic diagrams illustrating a further example of an absorbent article according to the present invention. FIG. 10(A) illustrates the state in which an absorbent article, in the form of an underpants-type diaper, is cut along the right and left side parts (denoted with "Z" and "Z'" in the figure) of the waist gather and in which stress is applied to the absorbent article such that it is pulled in the front-rear direction and the lateral direction to be developed into a substantially planar form. FIG. 10(B) is a lateral end view along line XB-XB in FIG. 10(A) in the state described above.

Absorbent article 112 shown in FIG. 10 is basically similar to absorbent article 100 shown in FIGS. 1 and 2; however, it differs therefrom with respect to the point that, instead of FLGs 14, FLG sheet 65 formed with FLGs 14*c* shown in FIG. 8 (B) is provided.

FLG sheet 65 includes, in one sheet, a front end part, a rear end part and a section that configures head parts 16 of the pair of right and left FLGs 14 therebetween.

The front end part of FLG sheet 65 is joined to the front end part of the absorbent article body by means of coupling parts 74. Similarly to the rear end part shown in FIG. 10(B), the right and left edge parts in the vicinity of the front end part couple to surface 12*s* of absorber 12 and are sealed such that no leakage occurs.

The rear end part of FLG sheet 65 is joined to the rear end part of the absorbent article body by means of coupling parts 78. As shown in FIG. 10(B), the right and left edge parts in the vicinity of the rear end part are coupled to surface 12*s* of absorber 12 and are sealed such that no leakage occurs.

Since FLG sheet 65 is joined along three sides including the front end part and the right and left edge parts described above, front part pocket 24", which is larger and deeper than front part pocket 24, is formed and also, since FLG sheet 65 is joined along three sides including the rear end part and the right and left edge parts described above, rear part pocket 26", which is larger and deeper than rear part pocket 26, is formed. In this way, leakage is more effectively prevented.

In absorbent article 112, the shape and size of front part pocket 24" and rear part pocket 26" are the same; however, the present invention is not limited thereto and the shape and size may be different.

As shown in FIG. 10(B), SLG 28 that extends outside of absorber 12 is folded back, on the inward side, so as to cover a side edge part of FLG sheet 65. A front end part and a rear end part of the head part (the part that includes no stretchable member) of SLG 28 are respectively coupled onto FLG sheet 65 at SLG coupling parts 72 and 76.

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

For example, a form in which the space between the opposing head parts of the pair of right and left FLGs is covered with means of a leak prevention sheet, at least partially in the front-rear direction, such as that shown in FIG. 9 and FIG. 10, and a form in which a hanging part support sheet is included, such as that shown in FIG. 4, may be combined.

The absorbent article according to the present invention may be preferably used for paper diapers (for infants and adults), incontinence articles, training pants, or the like.

DESCRIPTIONS OF REFERENCE NUMERALS 10, 10a leak preventer
11 covering sheet
12, 12a absorber
12s, 12as surface of the absorber
14, 14a, 14b, 14c, 14d floating leg gather (FLG)
16, 16a, 16b, 16c, 16d head part
18, 18a, 18b, 18c, 18d hanging part
20, 20a, 21, 21a, 66, 74 front coupling part
22, 22a, 23, 23a, 70, 78 rear coupling part
24, 24', 24", 24a front part pocket
25, 27 head part coupling part
26, 26', 26", 26a rear part pocket
28, 28a standing leg gather (SLG)
30 head part
32 leg part
48, 48a, 48b, 48c, 48d, 48e, 48f, 48g, 48h, 50, 50a, 50b, 50c, 50d, 50e, 50f, 50g coupling part
34, 64, 68, 72, 76 SLG coupling part
36 shining gather
38 waist gather
40, 40a top sheet
42 joining point
44 detachable member
46, 46a, 46b, 46c, 46d, 46e, 46f, 46g, 46h hanging part support sheet
52, 52a, 63 slit
54 notch
56 hydrophobic sheet
58 hydrophilic sheet
60 front part covering sheet
62 rear part covering sheet
65, 65a FLG sheet
100, 102, 104, 106, 108, 110, 112 absorbent article
C crotch part
F front body
Oc center opening
Of front part opening
Or rear part opening
P transferring passage for bodily fluids
R rear body

The invention claimed is:

1. An absorbent article including:
a body that includes a front body, a crotch part and a rear body arranged in this order in a length direction;
a leak preventer in sheet form;
an absorber capable of absorbing a bodily fluid, wherein at least one layer thereof is arranged above the leak preventer; and
a pair of right and left floating leg gathers that are arranged above the absorber, each having a front end part and a rear end part along the length direction,
wherein each floating leg gather has a head part and a hanging part, the hanging part has an upper end that connects to the head part, and a lower end that hangs down toward the absorber,
wherein the head parts of the pair of right and left floating leg gathers are arranged toward each other and the hanging parts thereof are arranged away from each other in a width direction,
wherein the front end part and the rear end part of each floating leg gather respectively couple to the absorber in the vicinity of the front body and in the vicinity of the rear body of the body of the absorbent article, the lower ends of the hanging parts being spaced apart from the body of the absorbent article and not being coupled to the body of the absorbent article in the vicinity of the crotch part,
wherein the pair of right and left floating leg gathers: (1) are coupled to the body of the absorbent article and/or to a surface of the absorber in the vicinity of lower end parts of the hanging parts thereof, from the respective front end parts to the front body in the length direction to form a front part pocket; (2) are coupled to the body of the absorbent article and/or the surface of the absorber in the vicinity of the lower end parts of the hanging parts thereof, from the respective rear end parts to the rear body in the length direction to form a rear part pocket; and (3) are spaced apart from the surface of the absorber in the vicinity of the crotch part.

2. The absorbent article according to claim 1, wherein the head parts of the pair of right and left floating leg gathers are arranged in the vicinity of a center part in the lateral direction, and the head parts of the pair of right and left floating leg gathers are opposed to each other.

3. The absorbent article according to claim 2, wherein a space between the head parts of the pair of right and left floating leg gathers is covered with a leak prevention sheet at least partially in the front-rear direction, the head parts being opposed.

4. The absorbent article according claim 3, wherein a part in which the space between the head parts of the pair of right and left floating leg gathers is covered is present at least from the front end part of the body of the absorbent article to the front body thereof.

5. The absorbent article according to claim 3, wherein a part in which the space between the head parts of the pair of right and left floating leg gathers is covered is present at least from the rear end part of the body of the absorbent article to the rear body thereof.

6. The absorbent article according to claim 1, wherein the head parts of the pair of right and left floating leg gathers are overlapped with each other, in the vicinity of a center part in the lateral direction, at least partially in the front-rear direction.

7. The absorbent article according claim 6, wherein
parts of the head parts of the pair of right and left floating leg gathers that overlap with each other in the vicinity of the center part in the lateral direction are present at least from the front end part of the body of the absorbent article to the front body thereof.

8. The absorbent article according claim 6, wherein
parts of the head parts of the pair of right and left floating leg gathers that overlap with each other in the vicinity of the center part in the lateral direction are present at least from the rear end part of the body of the absorbent article to the rear body thereof.

9. The absorbent article according to claim 1, wherein
the hanging parts of the pair of right and left floating leg gathers are connected to each other in the vicinity of the lower end part thereof in the vicinity of the crotch part, and a transferring passage for bodily fluids is formed on the inner surface sides of the hanging parts.

10. The absorbent article according to claim 9, wherein
the hanging parts of the pair of right and left floating leg gathers are connected to each other by being respectively coupled to a hanging part support sheet in the vicinity of the lower end parts thereof in the vicinity of the crotch part, and
the transferring passage for bodily fluids is formed by the hanging parts and the hanging part support sheet.

11. The absorbent article according to claim 9, wherein
the transferring passage for bodily fluids further extends from the crotch part to the front body.

12. The absorbent article according to claim 11, wherein
the transferring passage for bodily fluids connects to the front part pocket.

13. The absorbent article according to claim 9, wherein
the transferring passage for bodily fluids further extends from the crotch part to the rear body.

14. The absorbent article according to claim 13, wherein
the transferring passage for bodily fluids connects to the rear part pocket.

15. The absorbent article according to claim 9, wherein
the transferring passage for bodily fluids couples to the surface of the absorber at a front end part thereof and/or a rear end part thereof.

16. The absorbent article according to claim 1, further comprising a pair of right and left standing leg gathers which are arranged outward of the pair of right and left floating leg gathers, wherein
the standing leg gather has a head part and a leg part that continues to the head part, a lower end part of the leg part being coupled to the body of the absorbent article and standing up therefrom.

17. The absorbent article according to claim 16, wherein
the hanging part of the floating leg gather and the leg part of the standing leg gather are coupled to each other.

18. The absorbent article according to claim 17, wherein
a part where the hanging part of the floating leg gather and the leg part of the standing leg gather are coupled to each other is present at least in the rear body.

19. The absorbent article according to claim 17, wherein
a part where the hanging part of the floating leg gather and the leg part of the standing leg gather are coupled to each other is present at least in the vicinity of the crotch part.

* * * * *